US011014862B2

(12) United States Patent
Matsuo et al.

(10) Patent No.: US 11,014,862 B2
(45) Date of Patent: May 25, 2021

(54) CATALYST FOR HYDROGENATION OF CARBONYL COMPOUND AND ALCOHOL PRODUCTION METHOD

(71) Applicant: Mitsubishi Chemical Corporation, Chiyoda-ku (JP)

(72) Inventors: Takeshi Matsuo, Chiyoda-ku (JP); Yumiko Yoshikawa, Chiyoda-ku (JP); Takayuki Aoshima, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/563,609

(22) Filed: Sep. 6, 2019

(65) Prior Publication Data

US 2020/0001276 A1 Jan. 2, 2020

Related U.S. Application Data

(63) Continuation of application No. PCT/JP2018/008816, filed on Mar. 7, 2018.

(30) Foreign Application Priority Data

Mar. 8, 2017 (JP) .............................. JP2017-043988
May 23, 2017 (JP) ................................. 2017-102053

(51) Int. Cl.
| | | |
|---|---|---|
| *C07C 29/149* | (2006.01) | |
| *B01J 23/36* | (2006.01) | |
| *B01J 21/06* | (2006.01) | |
| *B01J 23/656* | (2006.01) | |
| *B01J 27/053* | (2006.01) | |
| *B01J 37/18* | (2006.01) | |
| *C07C 29/141* | (2006.01) | |
| *C07C 29/132* | (2006.01) | |
| *C07C 29/136* | (2006.01) | |
| *B01J 37/08* | (2006.01) | |

(52) U.S. Cl.
CPC ........... *C07C 29/149* (2013.01); *B01J 21/063* (2013.01); *B01J 23/36* (2013.01); *B01J 23/6567* (2013.01); *B01J 27/053* (2013.01); *B01J 37/18* (2013.01); *C07C 29/132* (2013.01); *C07C 29/136* (2013.01); *C07C 29/141* (2013.01); *B01J 37/08* (2013.01)

(58) Field of Classification Search
CPC ..... C07C 29/14; C07C 29/145; C07C 29/136; C07C 29/149; C07C 29/132; C07C 29/141; C07C 29/147; B01J 23/6567; B01J 23/36; B01J 27/053; B01J 21/063

See application file for complete search history.

(56) References Cited

U.S. PATENT DOCUMENTS

| | | | |
|---|---|---|---|
| 4,317,918 A * | 3/1982 | Takano | B01J 23/36 562/406 |
| 4,782,167 A | 11/1988 | Rao | |
| 6,376,414 B1 | 4/2002 | Antons et al. | |
| 6,670,490 B1 * | 12/2003 | Campos | B01J 23/6567 502/185 |
| 6,765,118 B2 * | 7/2004 | Fischer | B01J 23/36 568/799 |
| 7,378,356 B2 | 5/2008 | Zhang et al. | |
| 7,423,190 B2 | 9/2008 | Boldingh et al. | |
| 9,108,895 B2 | 8/2015 | Liu et al. | |
| 2007/0135648 A1 | 6/2007 | Urtel et al. | |
| 2008/0025903 A1 | 1/2008 | Cortright | |
| 2008/0216391 A1 | 9/2008 | Cortright et al. | |
| 2008/0300434 A1 | 12/2008 | Cortright et al. | |
| 2008/0300435 A1 | 12/2008 | Cortright et al. | |
| 2010/0288975 A1 | 11/2010 | Cortright et al. | |
| 2011/0105313 A1 | 5/2011 | Oudart et al. | |
| 2011/0245542 A1 | 10/2011 | Cortright et al. | |
| 2011/0245543 A1 | 10/2011 | Cortright et al. | |
| 2011/0257416 A1 | 10/2011 | Cortright et al. | |
| 2017/0022129 A1 * | 1/2017 | Salciccioli | B01J 23/06 |

FOREIGN PATENT DOCUMENTS

| | | | |
|---|---|---|---|
| JP | 63-218636 A | | 9/1988 |
| JP | 63-301845 A | | 12/1988 |
| JP | 4-99753 A | | 3/1992 |
| JP | 6-116182 A | | 4/1994 |
| JP | 6-179667 A | | 6/1994 |
| JP | 7-118187 A | | 5/1995 |
| JP | 2000-7596 A | | 1/2000 |

(Continued)

OTHER PUBLICATIONS

International Search Report dated Jun. 12, 2018 in PCT/JP2018/008816 filed Mar. 7, 2018.

(Continued)

*Primary Examiner* — Yate' K Cutliff

(74) *Attorney, Agent, or Firm* — Oblon, McClelland, Maier & Neustadt, L.L.P.

(57) ABSTRACT

Provided is a catalyst including a metal component including a first component that is rhenium and one or more second components selected from the group consisting of silicon, gallium, germanium, and indium and a carrier on which the metal component is supported, the carrier including an oxide of a metal belonging to Group 4 of the periodic table. Also provided is an alcohol production method in which a carbonyl compound is treated using the above catalyst. It is possible to produce an alcohol by a hydrogenation reaction of a carbonyl compound with high selectivity and high efficiency while reducing side reactions.

16 Claims, No Drawings

(56) References Cited

FOREIGN PATENT DOCUMENTS

| | | | |
|---|---|---|---|
| JP | 2000-342968 A | 12/2000 | |
| JP | 2001-157841 A | 6/2001 | |
| JP | 2001-334151 A | 12/2001 | |
| JP | 2001-334152 A | 12/2001 | |
| JP | 2002-501817 A | 1/2002 | |
| JP | 2003-528064 | 9/2003 | |
| JP | 2008-55413 A | 3/2008 | |
| JP | 2010-535703 A | 11/2010 | |
| JP | 2016-500697 A | 1/2016 | |
| WO | WO-2004043890 A2 * | 5/2004 | ........... C07C 29/149 |
| WO | WO2015/037536 A1 | 3/2015 | |
| WO | WO-2020022256 * | 1/2020 | ........... C07C 29/149 |

OTHER PUBLICATIONS

Bao Khanh LY, et al., "Effect of Addition Mode of Re in Bimetallic Pd-Re/TiO$_2$ Catalysts Upon the Selective Aqueous-Phase Hydrogenation of Succinic Acid to 1,4-Butanediol", Topics in Catalysis, 55, 2012, pp. 466-473.

H. Smith Broadbent, et al, "Rhenium and Its Compounds as Hydrogenation Catalysts", J of Organic Chemistry, vol. 24, 1959, pp. 1847-1854.

Bartosz Rozmyslowicz, et al., "Selective hydrogenation of fatty acids to alcohols over highly dispersed ReO$_x$/TiO$_2$ catalyst", Journal of Catalysis 328, 2015, pp. 197-207.

Takashi Toyao, et al., "TiO$_2$-Supported Re as a General and Chemoselective Heterogeneous Catalyst for Hydrogenation of Carboxylic Acids to Alcohols", CHEMISTRY A European Journal Communication, 23, 2017, pp. 1001-1006.

Yasuyuki Takeda, et al., "Characterization of Re-Pd/SiO$_2$ Catalysts for hydrogenation of Stearic Acid", ACS Catalysis, 5, 2015, pp. 7034-7047.

Extended European Search Report, Completion of the Search dated Jan. 11, 2021 in European Patent Application No. 18763417.5, citing documents AA and AX therein, 6 pages.

Lan Ma, et al., "Influence of Catalyst Pretreatment on Catalytic Properties and Performances of Ru-Re/SiO$_2$ in Glycerol Hydrogenolysis to Propanediols" Catalysis Today, vol. 149; 2010, pp. 148-156.

* cited by examiner

CATALYST FOR HYDROGENATION OF CARBONYL COMPOUND AND ALCOHOL PRODUCTION METHOD

TECHNICAL FIELD

The present invention relates specifically to a catalyst useful as a catalyst for hydrogenation of a carbonyl compound and an alcohol production method in which a carbonyl compound is hydrogenated using the catalyst.

BACKGROUND ART

Methods in which a carbonyl compound is hydrogenated to form a corresponding alcohol have long been known. For example, a common alcohol production method from an organic carboxylic acid is to esterify a carboxylic acid with a lower alcohol and subsequently perform reduction using an Adkins catalyst (copper chromite catalyst).

However, the production of an alcohol with a copper catalyst, which is commonly conducted under a severe condition such as a hydrogen pressure of 200 atmospheres or more, is an uneconomical process that consumes a large amount of energy for producing an alcohol and introduces various facility restrictions. Furthermore, since a copper catalyst is not capable of directly reducing an organic carboxylic acid, a carboxylic acid needs to be converted into a carboxylic acid ester before a reduction treatment is performed. Therefore, multistage reaction processes need to be conducted in order to produce an intended alcohol. This increases the complexity of the process.

Moreover, in the case where the above production method is used, it becomes considerably difficult to selectively produce a hydroxycarboxylic acid using, for example, a polyvalent carboxylic acid as a raw material by converting a part of the carboxylic acid functional groups into alcohol functional groups.

In contrast, a method in which a carboxylic acid is directly hydrogenated (reduced) in one stage and a corresponding alcohol is produced with high selectivity is an economically advantageous process. Even in the case where a polyvalent carboxylic acid is used as a raw material, it is possible to selectively produce a corresponding hydroxycarboxylic acid by appropriately controlling the reaction conditions.

There have been proposed various metal-supporting catalysts that include a noble metal belonging to Groups 8 to 10 of the periodic table as a catalytic activity component, for use in such a process. Examples of the metal-supporting catalysts include a catalyst produced by attaching palladium and rhenium to a carrier and subsequently performing a reduction treatment with hydrogen or the like (e.g., PTL 1 and NPL 1) and a catalyst produced by attaching ruthenium and tin to a carrier and subsequently performing a reduction treatment with hydrogen or the like (e.g., PTLs 2 and 3).

The above catalysts are suitable catalysts that have a high reaction activity and high reaction selectivity in the reduction of a carboxylic acid and/or a carboxylic acid ester. There has also been proposed a hydrogenation reaction of a particular carboxylic acid in which a cobalt catalyst that includes lanthanum and palladium, which is an example of the above-described catalysts, is used (e.g., PTL 4).

On the other hand, there have also been proposed catalysts that do not include any of the expensive noble metals belonging to Groups 8 to 10 of the periodic table. For example, a catalyst including rhenium that serves as a catalytic component has been reported since a long time ago (e.g., NPL 2). There has also been proposed a tin-containing rhenium catalyst for use in a hydrogenation reaction of a particular carboxylic acid (e.g., PTL 5).

Recently, there has been reported a method for selectively producing an intended alcohol under further mild conditions. In the production method, a metal-supporting catalyst including rhenium that serves as a catalytic activity component is used (e.g., NPLs 3 and 4).

However, since catalysts including rhenium that serves as a catalytic activity component have lower catalytic activity than catalysts including a noble metal, it is common to use, as a supported metal, rhenium in combination with a noble metal belonging to Groups 8 to 10 of the periodic table or to add cobalt, which belongs to Group 9 of the periodic table, to a carrier (e.g., PTLs 6, 7, 8, and 9 and NPL 5).

PTL 1: Japanese Unexamined Patent Application Publication No. 63-218636
PTL 2: Japanese Unexamined Patent Application Publication No. 2000-007596
PTL 3: Japanese Unexamined Patent Application Publication No. 2001-157841
PTL 4: Japanese Unexamined Patent Application Publication No. 63-301845
PTL 5: Japanese Unexamined Patent Application Publication No. 4-99753
PTL 6: Japanese Unexamined Patent Application Publication No. 6-116182
PTL 7: Japanese Unexamined Patent Application Publication (Translation of PCT Application) No. 2002-501817
PTL 8: Japanese Unexamined Patent Application Publication (Translation of PCT Application) No. 2016-500697
PTL 9: Japanese Unexamined Patent Application Publication No. 7-118187
NPL 1: Topics in Catalysis 55 (2012) 466-473
NPL 2: Journal of Organic Chemistry 24 (1959) 1847-1854
NPL 3: Journal of Catalysis 328 (2015) 197-207
NPL 4: Chemistry A European Journal 23 (2017) 1001-1006
NPL 5: ACS Catalysis 5 (2015) 7034-7047

SUMMARY OF INVENTION

Technical Problem

A catalyst including a noble metal belonging to Groups 8 to 10 of the periodic table which serves as a catalytic activity component, which is produced using an expensive noble metal, increases the costs of production of a catalyst. In addition, such a catalyst typically causes side reactions, such as a degradation reaction that involves decarboxylation, a defunctionalization reaction associated with dehydration and hydrogenation of the reaction product, and an esterification reaction of a carboxylic acid used as a raw material with an alcohol produced. Thus, it is necessary to reduce the above side reactions.

For example, as for a palladium metal-supporting catalyst containing rhenium, the addition of rhenium increases the rate of catalytic reaction in which succinic acid is converted into the hydride of succinic acid, that is, butanediol, as described in NPL 1. However, the above-described side reactions also occur, which reduce the productivity of the reaction product and increase the purification costs. In addition, the catalytic activity of such a catalyst is still at an insufficient level.

As for the catalysts that include a catalytic component, such as tin, in addition to a noble metal belonging to Groups 8 to 10 of the periodic table as proposed in PTLs 2 and 3, the addition of tin or the like increases reaction selectivity. However, the addition of such catalytic components may disadvantageously reduce catalytic activity. This results in a necessity to further use a large amount of expensive noble metal, such as platinum, and increases the costs of production of a catalyst.

The catalyst including rhenium that serves as a principal catalytic activity component allows a highly economical process to be realized in the sense that the catalyst does not include any expensive noble metal. However, such catalysts typically have lower activity than catalysts that include a noble metal. Moreover, an esterification reaction of a carboxylic acid used as a raw material with an alcohol produced is likely to occur due to high Lewis acidity of rhenium and, particularly at a later stage of the reaction, a defunctionalization reaction may significantly occur due to the dehydration and hydrogenation of the alcohol produced. This significantly reduces the selectivity of the alcohol that is to be produced.

An object of the present invention is to provide a highly economical alcohol production method that enables an intended alcohol to be produced at a high yield with high selectivity by the hydrogenation reaction of a carbonyl compound while reducing the above-described various side reactions to a sufficient degree.

Another object of the present invention is to provide a high-activity metal-supporting catalyst including rhenium which enables an intended alcohol to be produced at a high yield with high selectivity by the hydrogenation reaction of a carbonyl compound while reducing the side reactions and a method for producing such a metal-supporting catalyst.

Solution to Problem

The inventors of the present invention found that the above issues may be addressed by using a catalyst produced by attaching rhenium and a specific second component to a carrier when an alcohol is produced by the hydrogenation reaction of a carbonyl compound and consequently made the present invention.

The summary of the first aspect of the present invention (hereinafter, referred to as "first invention") is as follows.

[1-1] An alcohol production method in which an alcohol is produced from a carbonyl compound, the method comprising producing an alcohol by using a catalyst, the catalyst including a metal component including a first component that is rhenium and one or more second components selected from the group consisting of silicon, gallium, germanium, and indium and a carrier on which the metal component is supported, the carrier including an oxide of a metal belonging to Group 4 of the periodic table.

[1-2] The alcohol production method according to [1-1], wherein the mass ratio of elements that are the second components included in the catalyst to the rhenium element included in the catalyst is 0.1 or more and 10 or less.

[1-3] The alcohol production method according to [1-1] or [1-2], wherein the oxide of a metal belonging to Group 4 of the periodic table, the oxide being included in the catalyst, includes titanium oxide and/or zirconium oxide.

[1-4] The alcohol production method according to any one of [1-1] to [1-3], wherein the catalyst is a catalyst prepared by a method including a step in which the metal component is attached to a carrier including a sulfate ion.

[1-5] The alcohol production method according to [1-4], wherein the sulfate ion content in the carrier is 0.01% by mass or more and 10% by mass or less of the mass of the carrier.

[1-6] The alcohol production method according to any one of [1-1] to [1-5], wherein the sulfate ion content in the catalyst is 0.01% by mass or more and 10% by mass or less of the mass of the catalyst.

[1-7] A catalyst comprising a metal component including a first component that is rhenium and one or more second components selected from the group consisting of silicon, gallium, germanium, and indium, and a carrier on which the metal component is supported, the carrier including an oxide of a metal belonging to Group 4 of the periodic table.

[1-8] The catalyst according to [1-7], wherein the mass ratio of elements that are the second components to the rhenium element is 0.1 or more and 10 or less.

[1-9] The catalyst according to [1-7] or [1-8], wherein the oxide of a metal belonging to Group 4 of the periodic table includes titanium oxide and/or zirconium oxide.

[1-10] The catalyst according to any one of [1-7] to [1-9], wherein the sulfate ion content in the catalyst is 0.01% by mass or more and 10% by mass or less of the mass of the catalyst.

[1-11] The catalyst according to any one of [1-7] to [1-10], the catalyst being a catalyst used for hydrogenation of a carbonyl compound.

The summary of the second aspect of the present invention (hereinafter, referred to as "second invention") is as follows.

[2-1] An alcohol production method in which an alcohol is produced from a carbonyl compound, the method comprising producing an alcohol by using a catalyst, the catalyst including a metal component including a first component that is rhenium and one or more second components selected from the group consisting of silicon, gallium, germanium, and indium and a carrier on which the metal component is supported, the mass ratio of elements that are the second components to the rhenium element being 0.1 or more and 10 or less.

[2-2] The alcohol production method according to [2-1], wherein the second components of the catalyst include germanium.

[2-3] The alcohol production method according to [2-1] or [2-2], wherein the mass ratio of a metallic element belonging to Groups 8 to 10 of the periodic table to the rhenium element included in the catalyst, the metallic element being other than iron or nickel, is less than 0.2.

[2-4] The alcohol production method according to [2-3], wherein the metallic element belonging to Groups 8 to 10 of the periodic table, the metallic element being included in the catalyst, the metallic element being other than iron or nickel, includes ruthenium.

[2-5] The alcohol production method according to any one of [2-1] to [2-4], wherein the carrier is a carbonaceous carrier or a carrier including an oxide of a metal belonging to Group 4 of the periodic table.

[2-6] The alcohol production method according to any one of [2-1] to [2-5], wherein the catalyst is a catalyst prepared by a method including a step in which the metal component is attached to a carrier including a sulfate ion.

[2-7] The alcohol production method according to [2-6], wherein the sulfate ion content in the carrier is 0.01% by mass or more and 10% by mass or less of the mass of the carrier.

[2-8] The alcohol production method according to any one of [2-1] to [2-7], wherein the sulfate ion content in the catalyst is 0.01% by mass or more and 10% by mass or less of the mass of the catalyst.

[2-9] A catalyst comprising a metal component including a first component that is rhenium and one or more second components selected from the group consisting of silicon, gallium, germanium, and indium and a carrier on which the metal component is supported, the mass ratio of elements that are the second components to the rhenium element being 0.1 or more and 10 or less.

[2-10] The catalyst according to [2-9], wherein the second components include germanium.

[2-11] The catalyst according to [2-9] or [2-10], wherein the mass ratio of a metallic element belonging to Groups 8 to 10 of the periodic table to the amount of the rhenium element, the metallic element being other than iron or nickel, is less than 0.2.

[2-12] The catalyst according to [2-11], wherein the metallic element belonging to Groups 8 to 10 of the periodic table, the metallic element being other than iron or nickel, includes ruthenium.

[2-13] The catalyst according to any one of [2-9] to [2-12], wherein the carrier is a carbonaceous carrier or a carrier including an oxide of a metal belonging to Group 4 of the periodic table.

[2-14] The catalyst according to any one of [2-9] to [2-13], wherein the sulfate ion content in the catalyst is 0.01% by mass or more and 10% by mass or less.

[2-15] The catalyst according to any one of [2-9] to [2-14], the catalyst being a catalyst used for hydrogenation of a carbonyl compound.

[2-16] A method for producing a catalyst, the method comprising attaching a metal component including at least a first component that is rhenium and one or more second components selected from the group consisting of silicon, gallium, germanium, and indium to a carrier including a sulfate ion, the content of the sulfate ion in the carrier being 0.01% by mass or more and 10% by mass or less of the mass of the carrier.

Advantageous Effects of Invention

According to the first invention, there is provided an alcohol production method in which a carbonyl compound is reduced into an alcohol with high activity and high selectivity by using a reduction catalyst including rhenium that serves as a catalytic activity component, the catalyst further including one or more catalytic additive components selected from the group consisting of silicon, gallium, germanium, and indium and a carrier including an oxide of a metal belonging to Group 4 of the periodic table, the catalytic additive components being supported on the carrier. Also provided is the catalyst useful for producing an alcohol. Note that the term "periodic table" used herein refers to the long form of periodic table (Nomenclature of Inorganic Chemistry IUPAC Recommendations 2005).

The catalyst according to the first invention enables an increase in catalytic activity, which has been an issue for rhenium catalysts, to be achieved substantially without using noble metals belonging to Groups 8 to 10 of the periodic table. The catalyst according to the first invention also makes it possible to produce an alcohol from a carbonyl compound while reducing side reactions, such as the esterification reaction of a carboxylic acid used as a raw material with an alcohol produced and a defunctionalization reaction due to the dehydration and hydrogenation of the alcohol produced, which significantly occurs particularly at a later stage of the reaction, to a high degree. It becomes also possible to, in the case where a polyvalent carboxylic acid is used as a raw material, produce a hydroxycarboxylic acid with high selectivity by converting a part of the carboxylic acid functional groups into alcohol functional groups.

According to the second invention, there is provided an alcohol production method in which a carbonyl compound is reduced into an alcohol with high activity and high selectivity by using a reduction catalyst including rhenium that serves as a catalytic activity component, the catalyst further including one or more catalytic additive components selected from the group consisting of silicon, gallium, germanium, and indium at a predetermined elemental mass ratio and a carrier, the catalytic additive components being supported on the carrier. Also provided is the catalyst useful for producing an alcohol.

The catalyst according to the second invention enables an increase in catalytic activity, which has been an issue for rhenium catalysts, to be achieved substantially without using noble metals belonging to Groups 8 to 10 of the periodic table. The catalyst according to the second invention also makes it possible to produce an alcohol from a carbonyl compound while reducing side reactions, such as the esterification reaction of a carboxylic acid used as a raw material with an alcohol produced and a defunctionalization reaction due to the dehydration and hydrogenation of the alcohol produced, which significantly occurs particularly at a later stage of the reaction, to a high degree. It becomes also possible to, in the case where a polyvalent carboxylic acid is used as a raw material, produce a hydroxycarboxylic acid with high selectivity by converting a part of the carboxylic acid functional groups into alcohol functional groups.

DESCRIPTION OF EMBODIMENTS

Embodiments of the present invention are described below in detail. The elements described below are merely an example (typical example) of an aspect of the present invention. The present invention is not limited by the description and may be modified within the scope of the present invention.

In the present invention, catalytic components supported on a carrier (e.g., rhenium; one or more elements selected from the group consisting of silicon, gallium, germanium, and indium; and optional metal elements belonging to Groups 8 to 10 of the periodic table, such as ruthenium) may be referred to collectively as "metal components".

A material produced by attaching the metal components to a carrier may be referred to as "metal-supporting material".

A catalyst produced by reducing the metal-supporting material may be referred to as "metal-supporting catalyst".

In the present invention, the metal components supported on the carrier are the same as the metal components included in the catalyst.

The content of the supported metal in the catalyst can be determined by publicly known analysis methods, such as inductively coupled plasma mass spectrometry (ICP-MS), inductively coupled plasma atomic emission spectrometry (ICP-AES), atomic absorption spectrometry (AAS), and X-ray fluorescence analysis (XRF). In the case where ICP-MS, ICP-AES, and AAS are used, the sample is formed into a solution in a pretreatment conducted in combination with the analysis. The type of the analysis method used is not limited since an appropriate analysis method varies with the element subjected to the quantitative analysis, the concentration of the element, and the accuracy required for the analysis. In the present invention, the quantitative analysis of the supported metal included in the catalyst is conducted using inductively coupled plasma atomic emission spectrometry, atomic absorption spectrometry, or both inductively coupled plasma atomic emission spectrometry and atomic absorption spectrometry in order to determine the metal content in the catalyst.

The mass ratio between the metal components supported on the carrier is calculated on the basis of the metal components included in the catalyst as in the description of the method for determining the content of the supported metal in the catalyst. The mass ratio between the rhenium element and the second component element can be determined using publicly known analysis methods, such as inductively coupled plasma mass spectrometry (ICP-MS), inductively coupled plasma atomic emission spectrometry (ICP-AES), atomic absorption spectrometry (AAS), and X-ray fluorescence analysis (XRF), as in the description of the method for determining the content of the supported metal in the catalyst.

In the present invention "% by weight" and "% by mass" are synonymous with each other, and "element" and "atom" are synonymous with each other.

The catalyst according to the present invention can be suitably used as a hydrogenation catalyst when an alcohol is produced from a carbonyl compound.

In the present invention, a carbonyl compound is defined as a compound that includes a carbon-oxygen double bond (C=O), and an alcohol is defined as a compound produced by converting the carbonyl compound into an alcohol functional group (OH).

Therefore, in the present invention, in the case where a carbonyl compound used as a raw material includes a plurality of carbon-oxygen double bonds, a compound produced by converting at least one of the carbon-oxygen double bonds of the carbonyl compound into an alcohol functional group is defined as an alcohol.

[Catalyst According to First Invention]

A catalyst according to the first invention (hereinafter, may be referred to simply as "first catalyst") is a metal-supporting catalyst that includes a metal component and a carrier on which the metal component is supported. Specifically, the metal components including a first component that is rhenium and one or more second components selected from the group consisting of silicon, gallium, germanium, and indium are supported on a carrier including an oxide of a metal belonging to Group 4 of the periodic table.

The first catalyst is normally produced by reducing a metal-supporting material on which the metal component is supported with a reducing gas and then performing an oxidative stabilization treatment as needed.

<Metal Component>

The metal component supported on the metal-supporting catalyst according to the first invention includes a first component that is rhenium and one or more second components selected from the group consisting of silicon, gallium, germanium, and indium. Among these, the second components used in combination with rhenium are preferably one or more elements selected from the group consisting of silicon, germanium, and indium, are more preferably one or more elements that include indium and/or germanium, are further preferably one or more elements that include germanium, and are particularly preferably germanium.

As for the ratio between the amounts of the above essential components supported on the catalyst, the lower limit for the mass ratio of the second component elements that are one or more elements selected from the group consisting of silicon, gallium, germanium, and indium to the rhenium element is preferably 0.1 or more and is more preferably 0.5 or more, and the upper limit for the above mass ratio is preferably 10 or less, is more preferably 5 or less, is further preferably 3 or less, is particularly preferably 2 or less, and is most preferably 1 or less.

Appropriately selecting the types of the second components used in combination with rhenium and/or the proportion of the second components supported on the carrier increases the catalytic activity in a hydrogenation reaction of a carbonyl compound and makes it possible to produce an alcohol while reducing side reactions, such as the esterification reaction of a carboxylic acid used as a raw material with an alcohol produced and a defunctionalization reaction due to the dehydration and hydrogenation of the alcohol produced, which significantly occurs particularly at a later stage of the reaction, to a high degree. Using the above metal components in combination with one another enables the first catalyst to be handled in the air atmosphere. This increases ease of operation, such as transportation and storage of the catalyst and introduction of the catalyst to a reactor in the production of an alcohol.

Using the above metal components in combination with one another enables an increase in catalytic activity and an increase in reaction selectivity, which have been considered contradictory, to be both achieved presumably for the following reasons: the addition of the second components enables the electronic state of rhenium, which is a catalytic activity component of the hydrogenation catalyst, to be controlled to be in a state suitable for a reduction reaction of a carbonyl functional group; the absorptivity of reactive substrates onto the surface of the catalyst is enhanced due to the affinity of the reactive substrates for the second components; and the orientation of adsorption of the reactive substrates on the surface of the catalyst is controlled at a high degree.

Although the amount of rhenium supported on the first catalyst is not limited, the mass ratio of the rhenium element to the total mass of the metal-supporting catalyst is normally 0.5% by mass or more, is preferably 1% by mass or more, is more preferably 3% by mass or more, is normally 20% by mass or less, is preferably 10% by mass or less, and is more preferably 8% by mass or less. When the amount of rhenium supported on the catalyst is limited to be equal to or more than the lower limit, sufficiently high catalytic activity can be achieved. This prevents, for example, an increase in the volume of the reactor used. When the amount of rhenium supported on the catalyst is limited to be equal to or less than the upper limit, an increase in the cost of the catalyst can be limited. Furthermore, in such a case, coagulation of rhenium supported on the catalyst can be reduced. This reduces the side reactions, such as a degradation reaction involved by decarboxylation, a defunctionalization reaction associated with dehydration and hydrogenation of the reaction product, and an esterification reaction of a carboxylic acid used as a raw material with an alcohol produced, due to high Lewis acidity of rhenium. As a result, reaction selectivity can be further increased.

The first catalyst may further include, as needed, a third component that is a metal component other than the above metal components (i.e., rhenium and the second components) and that does not adversely affect the reactions conducted using the first catalyst, such as a reduction reaction. Examples of the other metal component include metal components belonging to Groups 8 to 10 of the periodic table except iron and nickel. Examples thereof include at least one metal selected from the group consisting of ruthenium, cobalt, rhodium, iridium, palladium, and platinum, which are capable of catalyzing hydrogenation.

Metals, such as iron and nickel, may elute and enter the catalyst when a metal reaction container made of SS, SUS, or the like becomes corroded in the preparation of the catalyst and/or the reaction. In the first invention, in the case where the eluted metal is precipitated on the catalyst and included in the catalyst, the metal is not defined as a metal component of the first catalyst. In the case of elution from a reaction container made of SUS, in addition to iron, the following metals may be detected in the catalyst in trace amounts at specific contents depending on the material used.

For example, when metals enter from SUS201, nickel, chromium, and manganese may be detected in addition to iron at specific contents. When metals enter from SUS202, nickel, chromium, and manganese may be detected in addition to iron at specific contents. When metals enter from SUS301, nickel and chromium may be detected in addition to iron at specific contents. When metals enter from SUS302, nickel and chromium may be detected in addition to iron at specific contents. When metals enter from SUS303, nickel, chromium, and molybdenum may be detected in addition to iron at specific contents. When metals enter from SUS304, nickel and chromium may be detected in addition to iron at specific contents. When metals enter from SUS305, nickel and chromium may be detected in addition to iron at specific contents. When metals enter from SUS316, nickel, chromium, and molybdenum may be detected in addition to iron at specific contents. When metals enter from SUS317, nickel, chromium, and molybdenum may be detected in addition to iron at specific contents. When metals enter from SUS329J1, nickel, chromium, and molybdenum may be detected in addition to iron at specific contents. When metals enter from SUS403, chromium may be detected in addition to iron at a specific content. When metals enter from SUS405, chromium and aluminum may be detected in addition to iron at specific contents. When metals enter from SUS420, chromium may be detected in addition to iron at a specific content. When metals enter from SUS430, chromium may be detected in addition to iron at a specific content. When metals enter from SUS430LX, chromium, titanium, or niobium may be detected in addition to iron at a specific content. When metals enter from SUS630, nickel, chromium, copper, and niobium may be detected in addition to iron at specific contents.

Examples of the metal component that belongs to a group other than Groups 8 to 10 of the periodic table include at least one metal selected from the group consisting of silver, gold, molybdenum, tungsten, aluminum, and boron.

Among the above third components, at least one metal selected from ruthenium, cobalt, rhodium, iridium, palladium, platinum, gold, molybdenum, and tungsten is preferable; at least one metal selected from ruthenium, cobalt, rhodium, iridium, palladium, platinum, molybdenum, and tungsten is more preferable; at least one metal selected from ruthenium, iridium, palladium, and platinum is particularly preferable; and ruthenium is most preferable.

In the case where the third component is selected from rare and expensive metals belonging to Groups 8 to 10 of the periodic table except iron and nickel, the elemental mass ratio of the third component included in the first catalyst to the rhenium element is normally less than 0.2, is preferably 0.15 or less, is more preferably 0.1 or less, is further preferably less than 0.1, and is most preferably 0 in order to increase reaction selectivity and economical efficiency in terms of the costs for producing the catalyst. That is, it is preferable that the first catalyst substantially do not include any of the rare and expensive metals belonging to Groups 8 to 10 of the periodic table other than iron or nickel.

In the case where the third component is selected from metals other than the noble metals belonging to Groups 8 to 10 of the periodic table, the elemental mass ratio of the third component to the rhenium element is normally 10 or less, is preferably 5 or less, is more preferably 1 or less, and is further preferably 0.5 or less. When the above additional metal components are used in an appropriate combination at adequate contents, it is possible to achieve high catalytic activity while maintaining high selectivity.

In the case where a metal, such as iron or nickel, becomes eluted and enters the catalyst due to the corrosion of a reaction container made of SS, SUS, or the like, in the first invention, the content of iron and the contents of the above metals included at specific contents, which are determined on the basis of the type of material constituting the reaction container, are not taken into account in the calculation of the content of the metal components in the catalyst.

In order to further increase the activity of the catalyst, reaction selectivity, and the like, the first catalyst may include compounds of one or more alkali metal elements selected from the group consisting of lithium, sodium, potassium, rubidium, and cesium; compounds of one or more alkaline-earth metal elements selected from the group consisting of magnesium, calcium, strontium, and barium; and compounds of one or more halogen elements selected from the group consisting of fluorine, chlorine, bromine, and iodine, in addition to the metal components described above. In such a case, the ratio between the additional components and the rhenium component is not limited.

<Carrier>

The carrier used in the first invention is a carrier that includes an oxide of a metal belonging to Group 4 of the periodic table. In particular, an inert carrier can be used. The term "inert carrier" used herein refers to a carrier that does not have a catalytic activity in a hydrogenation of a carbonyl compound alone. Specifically, the inert carrier is defined as a carrier that substantially does not include any of the metals belonging to Group 8 to 12 of the periodic table which is selected from the group consisting of iron, ruthenium, cobalt, rhodium, iridium, nickel, palladium, platinum, copper, and zinc, chromium, and rhenium, which are metals having catalytic activity.

A carrier that substantially does not include any of the above metals is a carrier that does not primarily include any of the above metals. That is, the amount of the above metals included in the carrier to the total mass of the carrier is 5% by mass or less, is preferably 1% by mass or less, and is more preferably 0.1% by mass or less. The content of the above metals in the carrier can be determined as in the analysis of the content of the supported metal in the catalyst, using publicly known analysis methods, such as inductively coupled plasma mass spectrometry (ICP-MS), inductively coupled plasma atomic emission spectrometry (ICP-AES), atomic absorption spectrometry (AAS), and X-ray fluorescence analysis (XRF).

In the first invention, a carrier that includes an oxide of a metal belonging to Group 4 of the periodic table, such as titanium oxide (titania), zirconium oxide (zirconia), or hafnium oxide, is used in order to increase catalytic activity and reaction selectivity achieved particularly when a carboxylic acid is used as a raw material and ease of regeneration of the catalyst and reduce the elution of metals. Among the oxides of metals belonging to Group 4 of the periodic table, titanium oxide and zirconium oxide are preferable in order to increase catalytic activity and produce an intended alcohol with high selectivity. Among these, titanium oxide may be particularly preferable in order to readily produce carrier particles having a large specific surface area. The oxides of metals belonging to Group 4 of the periodic table may be used alone or in combination of two or more. In the case where the oxides of metals belonging to Group 4 of the periodic table are used in combination of two or more, the combination of the oxides and the mixing ratio between the oxides are not limited. The oxides can be used in a form similar to a mixture of the individual compounds or a composite oxide.

It may be preferable that the carrier used in the first invention contain a sulfate ion. In particular, in the case where titanium oxide is used as a carrier, it may be preferable that the carrier contain a sulfate ion.

In the first invention, using a carrier including a sulfate ion may markedly reduce a degradation reaction involved by decarboxylation and a defunctionalization reaction associated with dehydration and hydrogenation of the reaction product, that is, an alcohol, which occur simultaneously with a catalytic reaction of hydrogenation of a carbonyl compound. In addition, when the metal components that include rhenium and the second components are supported on such a carrier, the catalytic activity of the hydrogenation catalyst may be markedly increased. When the metal components are used in combination with the carrier, the catalyst can be handled in the air atmosphere. This increases ease of operation of the catalyst, such as transportation and storage of the catalyst and introduction of the catalyst to a reactor in the production of an alcohol.

It is considered that the functions of the catalyst are enhanced for the following reasons: when the carrier contains a sulfate ion, sulfate ions present in the surface of the carrier may form acid sites on the surface of the catalyst. Furthermore, the dispersibility of the supported metal may be increased due to the interaction between the supported metal and the sulfate ion or a substitution reaction of the supported metal with the sulfate ion which occurs when the metal components are supported on the carrier. Moreover, the electronic state of rhenium, which is a catalytic activity component of the hydrogenation catalyst, can be controlled to be in a state suitable for a reduction reaction of a carbonyl functional group. The above factors may synergistically increase the reaction selectivity of the catalyst and the activity of the catalyst.

The mass ratio of the amount of the sulfate ion included in the carrier to the total mass of the carrier used is preferably 0.01% by mass or more, is more preferably 0.1% by mass or more, and is particularly preferably 0.2% by mass or more. The mass ratio of the amount of the sulfate ion to the total mass of the carrier used is preferably 10% by mass or less, is more preferably 7% by mass or less, and is particularly preferably 5% by mass or less.

When the content of the sulfate ion in the carrier used is limited to be equal to or more than the lower limit, the advantageous effects of adding the above components are achieved at a sufficient level and high catalytic activity can be achieved. Furthermore, the occurrence of the defunctionalization reaction can be further reduced. This limits an increase in the complexity of the process for purifying the reaction product and an increase in the purification costs and consequently enables an economically advantageous alcohol production process to be provided. Limiting the content of the sulfate ion in the carrier used to be equal to or less than the upper limit reduces, for example, corrosion of the reactor caused by sulfate ions included in the carrier becoming eluted during the reaction depending on the solvent used and side reactions of the target product caused by the liberated acid catalyst and therefore eliminates the need to use materials having high corrosion resistance. This limits increases in the costs for constructing reaction facilities and the costs for purifying the product and enables an economically advantageous alcohol production process to be provided.

In the case where a carrier including a sulfate ion is used in the first invention, the carrier is not limited and may be any carrier that includes a sulfate ion. An appropriate commercial product may be used directly. In the case where the carrier is composed of a metal oxide, the carrier may be prepared by, for example, dissolving a corresponding metal sulfate in water and subsequently performing neutralization or pyrohydrolysis, or by treating a corresponding metal hydroxide or a baked metal oxide with a sulfatizing agent and subsequently performing baking in an oxidizing atmosphere, such as the air atmosphere. The treatment using a sulfatizing agent is to introduce sulfate ions into the carrier. This treatment may be performed in the step of producing the carrier or may be performed after the production of the carrier. Examples of the sulfatizing agent include sulfuric acid, persulfuric acid, and the salts thereof. Sulfuric acid, a sulfuric acid salt, and a persulfuric acid salt are preferable. The sulfuric acid salt is not limited and may be any sulfuric acid salt capable of providing sulfate ions when dissolved. Examples of the sulfuric acid salt include ammonium sulfate, sodium sulfate, and potassium sulfate. The same applies to the persulfuric acid salt, and examples thereof include ammonium persulfate, sodium persulfate, and potassium persulfate. The above salts may be in the form of an anhydride or hydrate. Such salts may be preferable in some cases because they are less hazardous than acids and easy to handle.

A preparation example of the carrier including a sulfate ion according to the first invention is described below, taking titanium oxide and zirconium oxide as an example.

Titanium oxide containing a sulfate ion can be prepared by dissolving titanium sulfate or titanyl sulfate in water, subsequently performing neutralization at a low temperature or pyrohydrolysis, and then performing baking. Titanium oxide containing a sulfate ion can also be prepared by dissolving titanium ore in sulfuric acid, subsequently performing heating to produce metatitanic acid or titanium hydroxide, and then performing baking.

In another case, titanium oxide containing a sulfate ion may be produced by passing dilute sulfuric acid through titanium hydroxide, which is a starting material, prepared from titanium tetraisopropoxide or the like and subsequently performing baking in the air atmosphere. Alternatively, a baked titanium oxide may also be used as a starting material instead of titanium hydroxide. Instead of passing sulfuric acid, a sulfuric acid salt, such as ammonium sulfate, may be supported on the carrier.

The titanium oxide that has been subjected to the sulfatizing treatment is subsequently baked. The baking temperature is preferably 350° C. to 700° C. and is more preferably 450° C. to 600° C. It is not preferable to set the baking temperature to be excessively high because, if the baking temperature is excessively high, the sulfate ions included in the catalyst become volatilized and the surface area of the titanium oxide decreases disadvantageously. The amount of baking time during which the baking is performed is not limited. It is appropriate to set the baking time to about 3 hours.

Examples of a commercial product of the titanium oxide containing a sulfate ion include MC-50, MC-90, and MC-150 produced by Ishihara Sangyo Kaisha, Ltd., which are also described in Examples of the first invention below.

Zirconium oxide containing a sulfate ion can be prepared by, as in the preparation example of the titanium oxide, adding sulfuric acid, a sulfate, a persulfate, or the like to a starting material that is, for example, zirconium hydroxide prepared by adding ammonia water to an aqueous solution of a zirconium compound, such as zirconium oxychloride, zirconium oxynitrate, zirconium propoxide, or the like, and subsequently performing baking in the air atmosphere. Alternatively, a baked zirconium oxide may also be used instead of zirconium hydroxide. Instead of passing dilute sulfuric acid, a sulfuric acid, such as ammonium sulfate, may be supported on the carrier.

The zirconium oxide that has been subjected to the sulfatizing treatment is subsequently baked. The baking temperature is preferably 350° C. to 700° C. and is more preferably 450° C. to 600° C. It is not preferable to set the baking temperature to be excessively high because, if the baking temperature is excessively high, the sulfate ions included in the catalyst become volatilized and the surface area of the zirconium oxide decreases disadvantageously. The amount of baking time during which the baking is performed is not limited. It is appropriate to set the baking time to about 3 hours.

In the case where the carrier is a commercial carrier, the content of sulfate ion in the carrier has been published by the manufacturer, and the sulfate ion content falls within the above-described range of sulfate ion content specified in the first invention, the carrier is considered to correspond to the carrier according to the first invention. Examples of such a commercial carrier include MC-50, MC-90, and MC-150 produced by Ishihara Sangyo Kaisha, Ltd.

In the case where it is clear that the sulfur element component of the carrier is derived from a sulfate ion, alternatively, the content of sulfate ion in the carrier or catalyst may be determined using a publicly known high-frequency furnace combustion-infrared detection method (carbon sulfur analyzer) by combusting the catalyst in a high-frequency induction heating furnace under an oxygen atmosphere and converting the content of sulfur in the combustion gas into the mass of sulfate ion, which is determined by an infrared detection method.

In the case where the catalyst according to the first invention contains a sulfate ion, the content of the sulfate ion in the catalyst is not limited and the mass ratio of the amount of sulfate ion to the total mass of the catalyst is preferably 0.01% by mass or more, is more preferably 0.1% by mass or more, is particularly preferably 0.2% by mass or more, is normally 10% by mass or less, is preferably 7% by mass or less, is more preferably 5% by mass or less, is particularly preferably 2% by mass or less, and is most preferably 1% by mass or less. The mass ratio of the amount of sulfur element to the total mass of the catalyst is preferably 0.01% by mass or more, is more preferably 0.1% by mass or more, is normally 3% by mass or less, is preferably 2% by mass or less, is more preferably 1% by mass or less, and is particularly preferably 0.6% by mass or less.

Using a catalyst containing a sulfate ion or sulfur may markedly reduce a degradation reaction involved by decarboxylation and a defunctionalization reaction associated with dehydration and hydrogenation of the reaction product, that is, an alcohol, which occur simultaneously with a catalytic reaction of hydrogenation of a carbonyl compound. Limiting the content of sulfate ion in the catalyst to be equal to or more than the lower limit may increase catalytic activity to a sufficient degree and reduce the occurrence of the defunctionalization reaction to a sufficient degree. This limits an increase in the complexity of the process for purifying the reaction product and an increase in the purification costs and consequently enables an economically advantageous alcohol production process to be provided. Limiting the content of sulfate ion in the catalyst according to the present invention to be equal to or more than the lower limit also enhances the stability of the catalyst in the air atmosphere. This increases ease of operation of the catalyst, such as transportation and storage of the catalyst and introduction of the catalyst to a reactor in the production of an alcohol. Limiting the content of the sulfate ion in the catalyst to be equal to or less than the upper limit reduces, for example, corrosion of the reactor caused by sulfate ions included in the catalyst becoming eluted during the reaction and side reactions of the target product caused by the liberated acid catalyst. This limits increases in the costs for constructing reaction facilities and the costs for purifying the target product and enables an economically advantageous alcohol production process to be provided.

In the first invention, the content of the sulfate ion in the carrier or catalyst is determined by publicly known ion chromatography after the sulfate ion has been extracted from the catalyst in a pretreatment step.

The content of the sulfur in the carrier or catalyst is determined using a publicly known high-frequency furnace combustion-infrared detection method (carbon sulfur analyzer) by combusting the catalyst in a high-frequency induction heating furnace under an oxygen atmosphere and calculating the content of sulfur in the combustion gas by an infrared detection method.

The carrier used in the first invention is preferably composed primarily of the oxide of a metal belonging to Group 4 of the periodic table. The expression "composed primarily of" used herein means that the mass ratio of the oxide of a metal belonging to Group 4 of the periodic table to the total mass of the carrier is normally 50% by mass or more, is preferably 70% by mass or more, and is more preferably 90% to 100% by mass.

The carrier used in the first invention may include a carrier component other than the oxide of a metal belonging to Group 4 of the periodic table. Examples of the other carrier component include one or more compounds selected from graphite, active carbon, silicon carbide, silicon nitride, aluminum nitride, boron nitride, boron oxide, aluminum oxide (alumina), silicon oxide (silica), lanthanum oxide, cerium oxide, yttrium oxide, niobium oxide, magnesium silicate, calcium silicate, magnesium aluminate, calcium aluminate, aluminosilicate, aluminosilicophosphate, aluminophosphate, magnesium phosphate, calcium phosphate, strontium phosphate, apatite hydroxide (calcium hydroxyphosphate), apatite chloride, apatite fluoride, calcium sulfate, barium sulfate, and barium carbonate.

The specific surface area of the carrier particles used in the first invention varies by the type of the carrier used and is not limited. The specific surface area of the carrier particles used in the first invention is normally 50 $m^2/g$ or more, is preferably 80 $m^2/g$ or more, is more preferably 100 $m^2/g$ or more, is normally 3000 $m^2/g$ or less, and is preferably 2000 $m^2/g$ or less. In particular, in the first invention in which the oxide of a metal belonging to Group 4 of the periodic table is used, the specific surface area of the carrier particles is normally 50 $m^2/g$ or more, is preferably 80 $m^2/g$ or more, is more preferably 100 $m^2/g$ or more, is normally 1000 $m^2/g$ or less, and is preferably 800 $m^2/g$ or less. The larger the specific surface area of the carrier particles, the higher the catalytic activity. Therefore, carrier particles having a larger specific surface area are suitably used. The specific surface area of the carrier particles is generally calculated from the amount of nitrogen adsorbed on the carrier particles using the BET equation.

The shape and size of the carrier particles used in the first invention are not limited. When the shape of the carrier particles is converted into a spherical shape, the average particle size of the carrier is normally 0.1 µm or more, is preferably 1 µm or more, is more preferably 5 µm or more, is further preferably 50 µm or more, is normally 5 mm or less, and is preferably 4 mm or less. The particle size of the carrier is measured in accordance with Test sieving described in JIS Standard JIS 28815 (1994). In the case where the shape of a carrier particle is not spherical, the volume of the carrier particle is measured, the diameter of a spherical particle having the same volume as the carrier particle is calculated, and the diameter of the spherical particle is considered the diameter of the carrier particle. When the average particle size of the carrier falls within the above range, the activity of the catalyst per unit mass is increased, and ease of handling of the catalyst is further increased.

In the case where the reaction conducted using the first catalyst is a complete mixing reaction, the average particle size of the carrier is normally 0.1 µm or more, is preferably 1 µm or more, is more preferably 5 µm or more, is further preferably 50 µm or more, is normally 3 mm or less, and is preferably 2 mm or less. It is preferable to reduce the average particle size of the carrier because the smaller the average particle size of the carrier, the higher the activity of the catalyst per unit mass. However, setting the average particle size of the carrier to be excessively smaller than the above lower limit may make it difficult to separate the reaction liquid and the catalyst from each other.

In the case where the reaction conducted using the first catalyst is a fixed-bed reaction, the average particle size of the carrier is normally 0.5 mm or more and 5 mm or less, is preferably 4 mm or less, and is more preferably 3 mm or less. If the particle size of the carrier is excessively smaller than the above lower limit, it may become difficult to operate a reaction facility due to pressure difference. If the particle size of the carrier is excessively larger than the above upper limit, reaction activity may be reduced.

[Catalyst According to Second Invention]

A catalyst according to the second invention (hereinafter, may be referred to simply as "second catalyst") is a metal-supporting catalyst that includes a metal component and a carrier on which the metal component is supported. Specifically, the metal components including a first component that is rhenium and one or more second components selected from the group consisting of silicon, gallium, germanium, and indium are supported on a carrier. The mass ratio of the amount of the second components to the amount of rhenium is set to a predetermined value.

The second catalyst is normally produced by reducing a metal-supporting material on which the metal component is supported with a reducing gas and then performing an oxidative stabilization treatment as needed.

<Metal Component>

The metal component supported on the metal-supporting catalyst according to the second invention includes a first component that is rhenium and one or more second components selected from the group consisting of silicon, gallium, germanium, and indium. Among these, the second components used in combination with rhenium are preferably one or more elements selected from the group consisting of silicon, germanium, and indium, are more preferably one or more elements that include indium and/or germanium, are further preferably one or more elements that include germanium, and are particularly preferably germanium.

As for the ratio between the amounts of the above essential components supported on the catalyst, the lower limit for the mass ratio of the second component elements that are one or more elements selected from the group consisting of silicon, gallium, germanium, and indium to the rhenium element is preferably 0.1 or more and is more preferably 0.5 or more, and the upper limit for the above mass ratio is preferably 10 or less, is more preferably 5 or less, is further preferably 3 or less, is particularly preferably 2 or less, and is most preferably 1 or less.

Appropriately selecting the types of the second components used in combination with rhenium and/or the proportion of the second components supported on the carrier increases the catalytic activity in a hydrogenation reaction of a carbonyl compound and makes it possible to produce an alcohol while reducing side reactions, such as an esterification reaction of a carboxylic acid used as a raw material with an alcohol produced, and a defunctionalization reaction due to the dehydration and hydrogenation of the alcohol produced, which significantly occurs particularly at a later stage of the reaction, to a high degree. Using the above metal components in combination with one another enables the second catalyst to be handled in the air atmosphere. This increases ease of operation, such as transportation and storage of the catalyst and introduction of the catalyst to a reactor in the production of an alcohol.

Using the above metal components in combination with each other enables an increase in catalytic activity and an increase in reaction selectivity, which have been considered contradictory, to be both achieved presumably for the following reasons: the addition of the second components enables the electronic state of rhenium, which is a catalytic activity component of the hydrogenation catalyst, to be controlled to be in a state suitable for a reduction reaction of a carbonyl functional group; the absorptivity of reactive substrates onto the surface of the catalyst is enhanced due to the affinity of the reactive substrates for the second components; and the orientation of adsorption of the reactive substrates on the surface of the catalyst is controlled at a high degree.

Although the amount of rhenium supported on the second catalyst is not limited, the mass ratio of the rhenium element to the total mass of the metal-supporting catalyst is normally 0.5% by mass or more, is preferably 1% by mass or more, is more preferably 3% by mass or more, is normally 20% by mass or less, is preferably 10% by mass or less, and is more preferably 8% by mass or less. When the amount of rhenium supported on the catalyst is limited to be equal to or more than the lower limit, sufficiently high catalytic activity can be achieved. This prevents, for example, an increase in the size of the reactor used. When the amount of rhenium supported on the catalyst is limited to be equal to or less than the upper limit, an increase in the cost of the catalyst can be limited. Furthermore, in such a case, coagulation of rhenium supported on the catalyst can be reduced. This reduces the side reactions, such as a degradation reaction involved by decarboxylation, a defunctionalization reaction associated with dehydration and hydrogenation of the reaction product, and an esterification reaction of a carboxylic acid used as a raw material with an alcohol produced, due to high Lewis acidity of rhenium. As a result, reaction selectivity can be further increased.

The second catalyst may further include, as needed, a third component that is a metal component other than the above metal components (i.e., rhenium and the second components) and that does not adversely affect the reactions conducted using the second catalyst, such as a reduction reaction. Examples of the other metal component include metal components belonging to Groups 8 to 10 of the periodic table except iron and nickel. Examples thereof include at least one metal selected from the group consisting of ruthenium, cobalt, rhodium, iridium, palladium, and platinum, which are capable of catalyzing hydrogenation. Note that the term "periodic table" used herein refers to the long form of periodic table (Nomenclature of Inorganic Chemistry IUPAC Recommendations 2005).

Metals, such as iron and nickel, may elute and enter the catalyst when a metal reaction container made of SS, SUS, or the like becomes corroded in the preparation of the catalyst and/or the reaction. In the second invention, in the case where the eluted metal is precipitated on the catalyst and included in the catalyst, the metal is not defined as a metal component of the second catalyst. In the case of elution from a reaction container made of SUS, in addition to iron, the following metals may be detected in the catalyst in trace amounts at specific contents depending on the material used.

For example, when metals enter from SUS201, nickel, chromium, and manganese may be detected in addition to iron at specific contents. When metals enter from SUS202, nickel, chromium, and manganese may be detected in addition to iron at specific contents. When metals enter from SUS301, nickel and chromium may be detected in addition to iron at specific contents. When metals enter from SUS302, nickel and chromium may be detected in addition to iron at specific contents. When metals enter from SUS303, nickel, chromium, and molybdenum may be detected in addition to iron at specific contents. When metals enter from SUS304, nickel and chromium may be detected in addition to iron at specific contents. When metals enter from SUS305, nickel and chromium may be detected in addition to iron at specific contents. When metals enter from SUS316, nickel, chromium, and molybdenum may be detected in addition to iron at specific contents. When metals enter from SUS317, nickel, chromium, and molybdenum may be detected in addition to iron at specific contents. When metals enter from SUS329J1, nickel, chromium, and molybdenum may be detected in addition to iron at specific contents. When metals enter from SUS403, chromium may be detected in addition to iron at a specific content. When metals enter from SUS405, chromium and aluminum may be detected in addition to iron at specific contents. When metals enter from SUS420, chromium may be detected in addition to iron at a specific content. When metals enter from SUS430, chromium may be detected in addition to iron at a specific content. When metals enter from SUS430LX, chromium, titanium, or niobium may be detected in addition to iron at a specific content. When metals enter from SUS630, nickel, chromium, copper, and niobium may be detected in addition to iron at specific contents.

Examples of the metal component that belongs to a group other than Groups 8 to 10 of the periodic table include at least one metal selected from the group consisting of silver, gold, molybdenum, tungsten, aluminum, and boron.

Among the above third components, at least one metal selected from ruthenium, cobalt, rhodium, iridium, palladium, platinum, gold, molybdenum, and tungsten is preferable; at least one metal selected from ruthenium, cobalt, rhodium, iridium, palladium, platinum, molybdenum, and tungsten is more preferable; at least one metal selected from ruthenium, iridium, palladium, and platinum is particularly preferable; and ruthenium is most preferable.

In the case where the third component is selected from rare and expensive metals belonging to Groups 8 to 10 of the periodic table except iron and nickel, the elemental mass ratio of the third component included in the second catalyst to the rhenium element is normally less than 0.2, is preferably 0.15 or less, is more preferably 0.1 or less, is further preferably less than 0.1, and is most preferably 0 in order to increase reaction selectivity and economical efficiency in terms of the costs for producing the catalyst. That is, it is preferable that the second catalyst substantially do not include any of the rare and expensive metals belonging to Groups 8 to 10 of the periodic table other than iron or nickel.

In the case where the third component is selected from metals other than the noble metals belonging to Groups 8 to 10 of the periodic table, the elemental mass ratio of the third component to the rhenium element is normally 10 or less, is preferably 5 or less, is more preferably 1 or less, and is further preferably 0.5 or less. When the above additional metal components are used in an appropriate combination at adequate contents, it is possible to achieve high catalytic activity while maintaining high selectivity.

In the case where a metal, such as iron or nickel, becomes eluted and enters the catalyst due to the corrosion of a reaction container made of SS, SUS, or the like, in the second invention, the content of iron and the contents of the above metals included at specific contents, which are determined on the basis of the type of material constituting the reaction container, are not taken into account in the calculation of the content of the metal components in the catalyst.

In order to further increase the activity of the catalyst, reaction selectivity, and the like, the second catalyst may include compounds of one or more alkali metal elements selected from the group consisting of lithium, sodium, potassium, rubidium, and cesium; compounds of one or more alkaline-earth metal elements selected from the group consisting of magnesium, calcium, strontium, and barium; and compounds of one or more halogen elements selected from the group consisting of fluorine, chlorine, bromine, and iodine, in addition to the metal components described above. In such a case, the ratio between the additional components and the rhenium component is not limited.

<Carrier>

The carrier used in the second invention is not limited. In particular, an inert carrier can be used. The term "inert carrier" used herein refers to a carrier that does not have a catalytic activity in a hydrogenation of a carbonyl compound alone. Specifically, the inert carrier is defined as a carrier that substantially does not include any of the metals belonging to Group 8 to 12 of the periodic table which is selected from the group consisting of iron, ruthenium, cobalt, rhodium, iridium, nickel, palladium, platinum, copper, and zinc, chromium, and rhenium, which are metals having catalytic activity.

In the second invention, a carrier that substantially does not include any of the above metals is a carrier that does not primarily include any of the above metals. That is, the amount of the above metals included in the carrier to the total mass of the carrier is 5% by mass or less, is preferably 1% by mass or less, and is more preferably 0.1% by mass or less. The content of the above metals in the carrier can be determined as in the analysis of the content of the supported metal in the catalyst, using publicly known analysis methods, such as inductively coupled plasma mass spectrometry (ICP-MS), inductively coupled plasma atomic emission spectrometry (ICP-AES), atomic absorption spectrometry (AAS), and X-ray fluorescence analysis (XRF).

Examples of the inert carrier used in the second invention includes a carrier composed primarily of an element other than the metals belonging to Groups 8 to 12 of the periodic table, such as iron, ruthenium, cobalt, rhodium, iridium, nickel, palladium, platinum, copper, and zinc, chromium, or rhenium; a carrier composed primarily of a carbide, a nitride, an oxide, a hydroxide, a sulfuric acid salt, a carbonic acid salt, or a phosphoric acid salt of the element; and a carrier composed primarily of a mixture of the above substances. The expression "composed primarily of" used herein means that the mass ratio of the substance to the total mass of the carrier is normally 50% by mass or more, is preferably 70% by mass or more, and is more preferably 90% by mass or more.

Specific examples of the carrier according to the second invention include graphite, active carbon, silicon carbide, silicon nitride, aluminum nitride, boron nitride, boron oxide, aluminum oxide (alumina), silicon oxide (silica), titanium oxide (titania), zirconium oxide (zirconia), hafnium oxide, lanthanum oxide, cerium oxide, yttrium oxide, niobium oxide, magnesium silicate, calcium silicate, magnesium aluminate, calcium aluminate, aluminosilicate, aluminosilicophosphate, aluminophosphate, magnesium phosphate, calcium phosphate, strontium phosphate, apatite hydroxide (calcium hydroxyphosphate), apatite chloride, apatite fluoride, calcium sulfate, barium sulfate, and barium carbonate.

Among these, a carbonaceous carrier, titanium oxide, zirconium oxide, niobium oxide, and cerium oxide are preferable in order to increase catalytic activity and reaction selectivity achieved particularly when a carboxylic acid is used as a raw material and reduce the elution of metals. Among the above substances, titanium oxide, zirconium oxide, niobium oxide, and cerium oxide are preferable in order to increase ease of the regeneration treatment of the catalyst. Among the above substances, titanium oxide and zirconium oxide, which are oxides of metals belonging to Group 4 of the periodic table, are more preferable. Titanium oxide may be particularly preferable in order to readily produce carrier particles having a large specific surface area.

The above carriers may be used alone or in combination of two or more. In the case where the carriers are used in combination of two or more, the combination of the carriers and the mixing ratio between the carriers are not limited. The carriers can be used in a form similar to a mixture of the individual compounds, a composite compound, or a double salt.

The carrier may be used directly or may be subjected to a pretreatment in which the carrier particles are formed into a shape suitable for supporting the metal components thereon. For example, in the case where a carbonaceous carrier is used, the carbonaceous carrier may be subjected to a heating treatment using nitric acid before use, as described in Japanese Unexamined Patent Application Publication No. 10-71332. It is preferable to use the above method in order to enhance the dispersibility of the metal components on the carrier and thereby increase the activity of the catalyst.

It may be preferable that the carrier used in the second invention contain a sulfate ion. In particular, in the case where titanium oxide is used as a carrier, it may be preferable that the carrier contain a sulfate ion.

In the second invention, using a carrier including a sulfate ion may markedly reduce a degradation reaction involved by decarboxylation and a defunctionalization reaction associated with dehydration and hydrogenation of the reaction product, that is, an alcohol, which occur simultaneously with a catalytic reaction of hydrogenation of a carbonyl compound. In addition, when the metal components that include rhenium and the second components are supported on such a carrier, the catalytic activity of the hydrogenation catalyst may be markedly increased. When the metal components are used in combination with the carrier, the catalyst can be handled in the air atmosphere. This increases ease of operation of the catalyst, such as transportation and storage of the catalyst and introduction of the catalyst to a reactor in the production of an alcohol.

It is considered that the functions of the catalyst are enhanced for the following reasons: when the carrier contains a sulfate ion, sulfate ions present in the surface of the carrier may form acid sites on the surface of the catalyst. Furthermore, the dispersibility of the supported metal may be increased due to the interaction between the supported metal and the sulfate ion or a substitution reaction of the supported metal with the sulfate ion which occurs when the metal components are supported on the carrier. Moreover, the electronic state of rhenium, which is a catalytic activity component of the hydrogenation catalyst, can be controlled to be in a state suitable for a reduction reaction of a carbonyl functional group. The above factors may synergistically increase the reaction selectivity of the catalyst and the activity of the catalyst.

The mass ratio of the amount of the sulfate ion included in the carrier to the total mass of the carrier used is preferably 0.01% by mass or more, is more preferably 0.1% by mass or more, and is particularly preferably 0.2% by mass or more. The mass ratio of the amount of the sulfate ion to the total mass of the carrier used is preferably 10% by mass or less, is more preferably 7% by mass or less, and is particularly preferably 5% by mass or less.

When the content of the sulfate ion in the carrier used is limited to be equal to or more than the lower limit, the advantageous effects of adding the above components are achieved at a sufficient level and high catalytic activity can be achieved. Furthermore, the occurrence of the defunctionalization reaction can be further reduced. This limits an increase in the complexity of the process for purifying the reaction product and an increase in the purification costs and consequently enables an economically advantageous alcohol production process to be provided. Limiting the content of the sulfate ion in the carrier used to be equal to or less than the upper limit reduces, for example, corrosion of the reactor caused by sulfate ions included in the carrier becoming eluted during the reaction depending on the solvent used and side reactions of the target product caused by the liberated acid catalyst and therefore eliminates the need to use materials having high corrosion resistance. This limits increases in the costs for constructing reaction facilities and the costs for purifying the product and enables an economically advantageous alcohol production process to be provided.

In the case where a carrier including a sulfate ion is used in the second invention, the carrier is not limited and may be any carrier that includes a sulfate ion. An appropriate commercial product may be used directly. In the case where the carrier is composed of a metal oxide, the carrier may be prepared by, for example, dissolving a corresponding metal sulfate in water and subsequently performing neutralization or pyrohydrolysis, or by treating a corresponding metal hydroxide or a baked metal oxide with a sulfatizing agent and subsequently performing baking in an oxidizing atmosphere, such as the air atmosphere. The treatment using a sulfatizing agent is to introduce sulfate ions into the carrier. This treatment may be performed in the step of producing the carrier or may be performed after the production of the carrier. Examples of the sulfatizing agent include sulfuric acid, persulfuric acid, and the salts thereof. Sulfuric acid, a sulfuric acid salt, and a persulfuric acid salt are preferable. The sulfuric acid salt is not limited and may be any sulfuric acid salt capable of providing sulfate ions when dissolved. Examples of the sulfuric acid salt include ammonium sulfate, sodium sulfate, and potassium sulfate. The same applies to the persulfuric acid salt, and examples thereof include ammonium persulfate, sodium persulfate, and potassium persulfate. The above salts may be in the form of an anhydride or hydrate. Such salts may be preferable in some cases because they are less hazardous than acids and easy to handle.

A preparation example of the carrier including a sulfate ion according to the second invention is described below, taking titanium oxide and zirconium oxide as an example.

Titanium oxide containing a sulfate ion can be prepared by dissolving titanium sulfate or titanyl sulfate in water, subsequently performing neutralization at a low temperature or pyrohydrolysis, and then performing baking. Titanium oxide containing a sulfate ion can also be prepared by dissolving titanium ore in sulfuric acid, subsequently performing heating to produce metatitanic acid or titanium hydroxide, and then performing baking.

In another case, titanium oxide containing a sulfate ion may be produced by passing dilute sulfuric acid through titanium hydroxide, which is a starting material, prepared from titanium tetraisopropoxide or the like and subsequently performing baking in the air atmosphere. Alternatively, a baked titanium oxide may also be used as a starting material instead of titanium hydroxide. Instead of passing sulfuric acid, a sulfuric acid salt, such as ammonium sulfate, may be supported on the carrier.

The titanium oxide that has been subjected to the sulfatizing treatment is subsequently baked. The baking temperature is preferably 350° C. to 700° C. and is more preferably 450° C. to 600° C. It is not preferable to set the baking temperature to be excessively high because, if the baking temperature is excessively high, the sulfate ions included in the catalyst become volatilized and the surface area of the titanium oxide decreases disadvantageously. The amount of baking time during which the baking is performed is not limited. It is appropriate to set the baking time to about 3 hours.

Examples of a commercial product of the titanium oxide containing a sulfate ion include MC-50, MC-90, and MC-150 produced by Ishihara Sangyo Kaisha, Ltd., which are also described in Examples of the second invention below.

Zirconium oxide containing a sulfate ion can be prepared by, as in the preparation example of the titanium oxide, adding sulfuric acid, a sulfate, a persulfate, or the like to a starting material that is, for example, zirconium hydroxide prepared by adding ammonia water to an aqueous solution of a zirconium compound, such as zirconium oxychloride, zirconium oxynitrate, zirconium propoxide, or the like, and subsequently performing baking in the air atmosphere. Alternatively, a baked zirconium oxide may also be used instead of zirconium hydroxide. Instead of passing dilute sulfuric acid, a sulfuric acid, such as ammonium sulfate, may be supported on the carrier.

The zirconium oxide that has been subjected to the sulfatizing treatment is subsequently baked. The baking temperature is preferably 350° C. to 700° C. and is more preferably 450° C. to 600° C. It is not preferable to set the baking temperature to be excessively high because, if the baking temperature is excessively high, the sulfate ions included in the catalyst become volatilized and the surface area of the zirconium oxide decreases disadvantageously. The amount of baking time during which the baking is performed is not limited. It is appropriate to set the baking time to about 3 hours.

In the case where the carrier is a commercial carrier, the content of sulfate ion in the carrier has been published by the manufacturer, and the sulfate ion content falls within the above-described range of sulfate ion content specified in the second invention, the carrier is considered to correspond to the carrier according to the second invention. Examples of such a commercial carrier include MC-50, MC-90, and MC-150 produced by Ishihara Sangyo Kaisha, Ltd.

In the case where it is clear that the sulfur element component of the carrier is derived from a sulfate ion, alternatively, the content of sulfate ion in the carrier or catalyst may be determined using a publicly known high-frequency furnace combustion-infrared detection method (carbon sulfur analyzer) by combusting the catalyst in a high-frequency induction heating furnace under an oxygen atmosphere and converting the content of sulfur in the combustion gas into the mass of sulfate ion, which is determined by an infrared detection method.

In the case where the catalyst according to the second invention contains a sulfate ion, the content of the sulfate ion in the catalyst is not limited and the mass ratio of the amount of sulfate ion to the total mass of the catalyst is preferably 0.01% by mass or more, is more preferably 0.1% by mass or more, is particularly preferably 0.2% by mass or more, is normally 10% by mass or less, is preferably 7% by mass or less, is more preferably 5% by mass or less, is particularly preferably 2% by mass or less, and is most preferably 1% by mass or less. The mass ratio of the amount of sulfur element to the total mass of the catalyst is preferably 0.01% by mass or more, is more preferably 0.1% by mass or more, is normally 3% by mass or less, is preferably 2% by mass or less, is more preferably 1% by mass or less, and is particularly preferably 0.6% by mass or less.

Using a catalyst containing a sulfate ion or sulfur may markedly reduce a degradation reaction involved by decarboxylation and a defunctionalization reaction associated with dehydration and hydrogenation of the reaction product, that is, an alcohol, which occur simultaneously with a catalytic reaction of hydrogenation of a carbonyl compound. Limiting the content of sulfate ion in the catalyst to be equal to or more than the lower limit may increase catalytic activity to a sufficient degree and reduce the occurrence of the defunctionalization reaction to a sufficient degree. This limits an increase in the complexity of the process for purifying the reaction product and an increase in the purification costs and consequently enables an economically advantageous alcohol production process to be provided. Limiting the content of sulfate ion in the catalyst according to the present invention to be equal to or more than the lower limit also enhances the stability of the catalyst in the air atmosphere. This increases ease of operation of the catalyst, such as transportation and storage of the catalyst and introduction of the catalyst to a reactor in the production of an alcohol. Limiting the content of the sulfate ion in the catalyst to be equal to or less than the upper limit reduces, for example, corrosion of the reactor caused by sulfate ions included in the catalyst becoming eluted during the reaction and side reactions of the target product caused by the liberated acid catalyst. This limits increases in the costs for constructing reaction facilities and the costs for purifying the target product and enables an economically advantageous alcohol production process to be provided.

In the second invention, the content of the sulfate ion in the carrier or catalyst is determined by publicly known ion chromatography after the sulfate ion has been extracted from the catalyst in a pretreatment step.

The content of the sulfur in the carrier or catalyst is determined using a publicly known high-frequency furnace combustion-infrared detection method (carbon sulfur analyzer) by combusting the catalyst in a high-frequency induction heating furnace under an oxygen atmosphere and calculating the content of sulfur in the combustion gas by an infrared detection method.

The specific surface area of the carrier particles used in the second invention varies by the type of the carrier used and is not limited. The specific surface area of the carrier particles used in the second invention is normally 50 $m^2/g$ or more, is preferably 80 $m^2/g$ or more, is more preferably 100 $m^2/g$ or more, is normally 3000 $m^2/g$ or less, and is preferably 2000 $m^2/g$ or less. In the case where a metal oxide is used as a carrier, the specific surface area of the carrier particles is normally 50 $m^2/g$ or more, is preferably 80 $m^2/g$ or more, is more preferably 100 $m^2/g$ or more, is normally 1000 $m^2/g$ or less, and is preferably 800 $m^2/g$ or less. The larger the specific surface area of the carrier particles, the higher the catalytic activity. Therefore, carrier particles having a larger specific surface area are suitably used. The specific surface area of the carrier particles is generally calculated from the amount of nitrogen adsorbed on the carrier particles using the BET equation.

The shape and size of the carrier particles used in the second invention are not limited. When the shape of the carrier particles is converted into a spherical shape, the average particle size of the carrier is normally 0.1 µm or more, is preferably 1 µm or more, is more preferably 5 µm or more, is further preferably 50 µm or more, is normally 5 mm or less, and is preferably 4 mm or less. The particle size of the carrier is measured in accordance with Test sieving described in JIS Standard JIS 28815 (1994). In the case where the shape of a carrier particle is not spherical, the volume of the carrier particle is measured, the diameter of a spherical particle having the same volume as the carrier particle is calculated, and the diameter of the spherical particle is considered the diameter of the carrier particle. When the average particle size of the carrier falls within the above range, the activity of the catalyst per unit mass is increased, and ease of handling of the catalyst is further increased.

In the case where the reaction conducted using the second catalyst is a complete mixing reaction, the average particle size of the carrier is normally 0.1 µm or more, is preferably 1 µm or more, is more preferably 5 µm or more, is further preferably 50 µm or more, is normally 3 mm or less, and is preferably 2 mm or less. It is preferable to reduce the average particle size of the carrier because the smaller the average particle size of the carrier, the higher the activity of the catalyst per unit mass. However, setting the average particle size of the carrier to be excessively smaller than the above lower limit may make it difficult to separate the reaction liquid and the catalyst from each other.

In the case where the reaction conducted using the second main catalyst is a fixed-bed reaction, the average particle size of the carrier is normally 0.5 mm or more and 5 mm or less, is preferably 4 mm or less, and is more preferably 3 mm or less. If the particle size of the carrier is excessively smaller than the above lower limit, it may become difficult to operate a reaction facility due to pressure difference. If the particle size of the carrier is excessively larger than the above upper limit, reaction activity may be reduced.

[Method for Producing this Catalyst]

The method for producing the first catalyst and the second catalyst (hereinafter, they are referred to as "this catalyst") normally includes the following steps.

(i) a step in which the metal components are attached to the carrier (hereinafter, this step is referred to as "metal attachment step"))
(ii) a step in which the resulting metal-supporting material is subjected to a reduction treatment using a reducing gas (hereinafter, this step is referred to as "reduction treatment step"))
(iii) a step in which oxidation is performed as needed subsequent to the reduction treatment (hereinafter, this step is referred to as "oxidative stabilization step"))

Each of the above steps is described below.

<(i) Metal Attachment Step>

The metal attachment step is a step in which required amounts of the above-described metal components are attached to the above-described carrier in order to prepare a metal-supporting material. The method for attaching the metal components to the carrier is not limited, and publicly known methods can be used. For attaching the metal components to the carrier, a solution or dispersion liquid containing metal-containing compounds that are raw materials for the metal components can be used.

The method for attaching the metal components to the carrier is not limited. Normally, various impregnation methods may be used. Examples thereof include an adsorption method in which metal ions are caused to adsorb to the carrier in an amount equal to or less than the saturation amount of the metal ions adsorbed by using the ability of the metal ions to adsorb to the carrier; an equilibrium adsorption method in which the carrier is immersed in the solution containing an amount of metal ions which is equal to or more than the saturation amount of the metal ions adsorbed and the excess solution is removed; a pore-filling method in which the solution having the same volume as the pores formed in the carrier is added to the carrier and the whole amount of the solution is caused to adsorb to the carrier; an incipient wetness method in which the solution is added to the carrier until the volume of the solution added is appropriate to the water absorption capacity of the carrier and the treatment is terminated when the surfaces of the carrier particles become uniformly wet and excess solution is not present on the surfaces of the carrier particles; an evaporation-to-dryness method in which the carrier is impregnated with the solution and the solvent is removed by evaporation while the solution is stirred; and a spray method in which the carrier is dried and the solution is sprayed to the dried carrier. Among these, the pore-filling method, the incipient wetness method, the evaporation-to-dryness method, and the spray method are preferable, and the pore-filling method, the incipient wetness method, and the evaporation-to-dryness method are more preferable. Using the above preparation methods enables rhenium, the above-described second component, and the optional third component and the other metal components which may be added to the catalyst as needed to be supported on the carrier while being relatively uniformly dispersed on the carrier. As described in the first and second inventions above, it may be preferable that the carrier include a sulfate ion. In such a case, it is preferable to attach the metal components to a carrier that includes an amount of sulfate ion which is 0.01% by mass or more and 10% by mass or less of the mass of the carrier.

The metal-containing compounds used are not limited and may be selected appropriately in accordance with the attaching method used. Examples thereof include halides, such as a chloride, a bromide, and an iodide; mineral acid salts, such as a nitric acid salt and a sulfuric acid salt; metal hydroxides; metal oxides; metal-containing ammonium salts; organic-group-containing compounds, such as an acetic acid salt and a metal alkoxide; and metal complexes. Among these, halides, mineral acid salts, metal hydroxides, metal oxides, metal-containing ammonium salts, and organic-group-containing compounds are preferable, and halides, mineral acid salts, metal oxides, metal-containing ammonium salts, and organic-group-containing compounds are more preferable. The above compounds may be used alone or in combination of two or more in a required amount.

When the metal-containing compounds are attached to the carrier, the metal-containing compounds may be dissolved or dispersed in a solvent and the resulting solutions and dispersion liquids may be used in any of the above attaching methods. The type of the solvent used in this step is not limited and may be any type of solvent in which the metal-containing compounds can be dissolved or dispersed and which does not adversely affect the baking and hydrogen reduction of the metal-supporting material and the hydrogenation reaction in which this catalyst is used, which are conducted in the subsequent step. Examples of the solvent include ketone solvents, such as acetone, alcohol solvents, such as methanol and ethanol, ether solvents, such as tetrahydrofuran and ethylene glycol dimethyl ether, and water. The above solvents may be used alone or in the form of a mixed solvent. Among the above solvents, water is preferably used because water is inexpensive and the solubility of the raw materials, that is, the metal-containing compounds, in water is high.

When the metal-containing compounds are dissolved or dispersed in the solvent, various additives may be optionally used in addition to the solvent. For example, using a solution of carboxylic acid and/or a carbonyl compound may improve the dispersibility of each of the metal components on the carrier which is achieved when the metal components are attached to the carrier, as described in Japanese Unexamined Patent Application Publication No. 10-15388.

The metal-supporting material may be dried as needed. It is preferable to subject the metal-supporting material to a reduction treatment step after the metal-supporting material has been dried and subsequently baked as needed, for the following reason: if the metal-supporting material is subjected to the subsequent reduction treatment without being dried, the catalyst may have low reaction activity.

The method for drying the metal-supporting material is not limited and may be any method capable of removing the solvent and the like used for attaching the metal components to the carrier. Normally, the metal-supporting material is dried in a stream of inert gas or at a reduced pressure.

The pressure at which the metal-supporting material is dried is not limited. Normally, the metal-supporting material is dried at normal pressure or a reduced pressure.

The temperature at which the metal-supporting material is dried is normally, but not limited to, 300° C. or less, is preferably 250° C. or less, is more preferably 200° C. or less, and is normally 80° C. or more.

After the metal-supporting material has been dried, the metal-supporting material may be baked as needed. Baking the metal-supporting material increases the likelihood of the catalyst having a high catalytic activity and excellent reaction selectivity. The baking of the metal-supporting material may be performed in the air atmosphere. For example, the baking of the metal-supporting material may be performed by heating the metal-supporting material in an air stream at a predetermined temperature for a predetermined amount of time.

The temperature at which the metal-supporting material is baked is normally, but not limited to, 100° C. or more, is preferably 250° C. or more, is more preferably 400° C. or more, is normally 1000° C. or less, is preferably 700° C. or less, and is more preferably 600° C. or less. The amount of time during which the metal-supporting material is baked, which varies with the baking temperature, is normally 30 minutes or more, is preferably 1 hour or more, is more preferably 2 hours or more, is normally 40 hours or less, is preferably 30 hours or less, and is more preferably 10 hours or less.

<(ii) Reduction Treatment Step>

The metal-supporting material is normally subjected to a reduction treatment using a reducing gas. In the reduction treatment, a publicly known method, such as liquid-phase reduction or a gas-phase reduction, may be used.

The reducing gas used in the reduction treatment step is not limited and may be any gas having a reducing power. Examples of the reducing gas include hydrogen, methanol, and hydrazine. The reducing gas is preferably hydrogen.

In the case where a hydrogen-containing gas is used as a reducing gas, the hydrogen concentration in the hydrogen-containing gas is not limited. The hydrogen concentration in the hydrogen-containing gas may be 100% by volume. In another case, the hydrogen-containing gas may be diluted with an inert gas. The term "inert gas" used herein refers to a gas unreactive with the metal-supporting material or a hydrogen gas, such as nitrogen or water vapor. Normally, nitrogen is used as an inert gas. The hydrogen concentration in the reducing gas (hydrogen-containing gas) diluted with an inert gas is normally 5% by volume or more, is preferably 15% by volume or more, is more preferably 30% by volume or more, and is further preferably 50% by volume or more relative to the all the gas components. It is possible to use a hydrogen-containing gas having a low hydrogen concentration at the initial stage of reduction and gradually increase the hydrogen concentration in the hydrogen-containing gas over the course of reduction.

The amount of time required for the reduction treatment, which varies with the amounts of the metal-supporting material and the like that are to be treated and the type of the apparatus or the like used, is normally 7 minutes or more, is preferably 15 minutes or more, is more preferably 30 minutes or more, is normally 40 hours or less, is preferably 30 hours or less, and is more preferably 10 hours or less. The temperature at which the reduction treatment is performed is normally 100° C. or more, is preferably 200° C. or more, is more preferably 250° C. or more, is normally 700° C. or less, is preferably 600° C. or less, and is more preferably 500° C. or less. If the reduction treatment is performed at an excessively high temperature, for example, the supported metal may become sintered and, consequently, the activity of the catalyst may be reduced.

In the reduction treatment, the reducing gas may be enclosed in the reactor or may be passed through the reactor. It is preferable to pass the reducing gas through the reactor. This is because passing the reducing gas through the reactor prevents the occurrence of local hydrogen deficiency. In the reduction treatment, water, ammonium chloride, and the like may be produced as by-products in the rector depending on the raw materials used, and the by-products may adversely affect the metal-supporting material that has not been subjected to the reduction treatment or the metal-supporting catalyst, which has been subjected to the reduction treatment. Passing the reducing gas through the reactor enables the by-products to be discharged to the outside of the reaction system.

The amount of the reducing gas required by the reduction treatment is not limited and may be set such that the objects of the first to third inventions are achieved. The amount of the reducing gas required by the reduction treatment can be set appropriately in accordance with the apparatus used, the size of the reactor used for reduction, the method for passing the reducing gas through the reactor, the method for fluidizing the catalyst, and the like.

The size of the metal-supporting catalyst, which has been subjected to the reduction treatment, is not limited and basically the same as the size of the carrier.

Examples of a preferable method for performing the reduction treatment include a method in which the reducing gas is passed through the metal-supporting material with a fixed bed; a method in which the reducing gas is passed through the metal-supporting material that is disposed to stand on a tray or a belt; and a method in which the metal-supporting material is caused to fluidize and the reducing gas is passed through the fluidized metal-supporting material.

<(iii) Oxidative Stabilization Step>

In the production of this catalyst, as needed, the metal-supporting catalyst, which is produced by reducing the metal-supporting material, is subjected to an oxidative stabilization treatment in order to control the oxidation state. Performing the oxidative stabilization treatment enables the production of a catalyst that has excellent activity and excellent selectivity and that can be handled in the air atmosphere.

The method for performing oxidative stabilization is not limited. Examples thereof include a method in which water is added to the metal-supporting catalyst, a method in which the metal-supporting catalyst is charged into water, a method in which oxidative stabilization is performed using a gas having a low oxygen concentration which is diluted with an inert gas, and a method in which stabilization is performed using carbon dioxide. Among the above methods, the method in which water is added to the metal-supporting catalyst, the method in which the metal-supporting catalyst is charged into water, and the method in which oxidative stabilization is performed using the gas having a low oxygen concentration are preferable, the method in which oxidative stabilization (slow oxidation) is performed using the gas having a low oxygen concentration (hereinafter, this method is referred to as "slow-oxidation method") is more preferable, and a method in which oxidative stabilization is performed in a stream of the gas having a low oxygen concentration is particularly preferable.

The initial oxygen concentration with which oxidative stabilization is performed using the gas having a low oxygen concentration is not limited. The oxygen concentration with which the slow oxidation is started is normally 0.2% by volume or more, is preferably 0.5% by volume or more, is normally 10% by volume or less, is preferably 8% by volume or less, and is further preferably 7% by volume or less. If the oxygen concentration is excessively lower than the lower limit, it takes a considerable amount of time to complete the oxidative stabilization and stabilization may fail to be achieved at a sufficient level. If the oxygen concentration is excessively higher than the upper limit, the temperature of the catalyst may be excessively increased and the catalyst may become deactivated.

The gas having a low oxygen concentration is preferably prepared by diluting air with an inert gas. The inert gas used for diluting air is preferably nitrogen.

Examples of a method for performing the oxidative stabilization using the gas having a low oxygen concentration include a method in which the gas having a low oxygen concentration is passed through the catalyst with a fixed bed; a method in which the gas having a low oxygen concentration is passed through the catalyst that is disposed to stand on a tray or a belt; and a method in which the catalyst is caused to fluidize and the gas having a low oxygen concentration is passed through the fluidized catalyst.

The higher the dispersibility of the supported metal on the metal-supporting catalyst, the higher the rate at which the oxidative stabilization is performed and the larger the amount of oxygen used in the reaction. Therefore, the method in which the gas having a low oxygen concentration is passed through the catalyst with a fixed bed and the method in which the catalyst is caused to fluidize and the gas having a low oxygen concentration is passed through the fluidized catalyst are preferable.

The method for producing this catalyst is not limited to the above-described production method and may be any method capable of producing this catalyst. For example, the method for producing this catalyst may include another publicly known step such that this catalyst can be produced.

[Production of Alcohol with this Catalyst]

This catalyst is suitable as a catalyst used in the reduction reaction (hydrogenation) of a carbonyl compound. An alcohol can be produced by treating a carbonyl compound with this catalyst.

Preferable examples of the reduction reaction conducted with this catalyst include an alcohol production method which includes a step in which at least one carbonyl compound selected from the group consisting of a ketone, an aldehyde, a carboxylic acid, a carboxylic acid ester, a carboxylic acid amide, a carboxylic acid halide, and a carboxylic anhydride is reduced to produce an alcohol derived from the compound. Among the above compounds, a carboxylic acid can be directly reduced with this catalyst to form an alcohol.

The carbonyl compound that is to be subjected to the reduction reaction may be any carbonyl compound that is industrially readily available. Specific examples of the carboxylic acid and/or the carboxylic acid ester include aliphatic chain monocarboxylic acids, such as acetic acid, butyric acid, decanoic acid, lauric acid, oleic acid, linoleic acid, linolenic acid, stearic acid, and palmitic acid; aliphatic cyclic monocarboxylic acids, such as cyclohexanecarboxylic acid, naphthenic acid, and cyclopentanecarboxylic acid; aliphatic polycarboxylic acids, such as oxalic acid, malonic acid, succinic acid, methylsuccinic acid, glutaric acid, adipic acid, pimelic acid, suberic acid, sebacic acid, cyclohexanedicarboxylic acid, 1,2,4-butanetricarboxylic acid, 1,3,4-cyclohexanetricarboxylic acid, bicyclohexyldicarboxylic acid, and decahydronaphthalenedicarboxylic acid; aromatic carboxylic acids, such as phthalic acid, isophthalic acid, terephthalic acid, and trimesic acid; carboxylic acids including a furan skeleton, such as furancarboxylic acid and furandicarboxylic acid; carboxylic acid esters, such as methyl esters, ethyl esters, propyl esters, and butyl esters of the above carboxylic acids and esters of an alcohol produced by reducing a carboxylic acid; and lactones, such as γ-butyrolactone, δ-valerolactone, and ε-caprolactone.

Specific examples of the carboxylic acid amide include methyl amides and ethyl amides of the above carboxylic acids.

Specific examples of the carboxylic acid halide include chlorides and bromides of the above carboxylic acids.

Specific examples of the carboxylic anhydride include acetic anhydride, succinic anhydride, maleic anhydride, and phthalic anhydride.

Examples of the aldehyde and the ketone include benzaldehyde, propionaldehyde, acetaldehyde, 3-hydroxypropionaldehyde, furfural, hydroxµmethylfurfural, acetone, benzophenone, glucose, xylose, lactose, and fructose.

The carboxylic acid and carboxylic acids constituting the carboxylic acid ester, the carboxylic acid amide, the carboxylic acid halide, and/or the carboxylic anhydride are preferably, but not limited to, chain or cyclic saturated aliphatic carboxylic acids, are more preferably carboxylic acids a portion of which excluding carboxyl groups has 20 or less carbon atoms. The number of the carbon atoms included in the carboxylic acids is more preferably 14 or less.

In the present invention, among the above carbonyl compounds that are to be subjected to the reduction reaction, the carboxylic acid, the carboxylic acid ester, the carboxylic anhydride, and the aldehyde are preferable, the carboxylic acid, the carboxylic acid ester, the carboxylic anhydride, and the aldehyde are more preferable, and the carboxylic acid and the carboxylic acid ester are particularly preferable from the viewpoint of ease of availability of the raw materials. However, the carbonyl compounds that are to be subjected to the reduction reaction are not limited to the above carbonyl compounds.

The carboxylic acid is preferably a dicarboxylic acid and is further preferably a dicarboxylic acid represented by Formula (1) below the portion of which except carboxyl groups includes 20 or less carbon atoms.

HOOC—R¹—COOH    (2)

(in Formula (1), $R^1$ represents an aliphatic or alicyclic hydrocarbon group that may have a substituent, the portion of the hydrocarbon group except the substituent including 1 to 20 carbon atoms)

This catalyst enables a polyvalent carboxylic acid, such as the above dicarboxylic acid, to be converted into a corresponding hydroxycarboxylic acid, lactone, or polyhydric alcohol with high selectivity at a high yield.

Appropriately selecting the production conditions, such as the type of catalyst used, the reaction pressure, the reaction temperature, and the amount of time the raw materials are retained, enables the ratio between the amount of the hydroxycarboxylic acid or lactone produced and the amount of the polyhydric alcohol produced to be controlled.

Other examples of particularly preferable carbonyl compounds include carboxylic acids having a furan skeleton which are derived from biomass resources, such as furandicarboxylic acid, and aldehydes, such as hydroxµmethylfurfural.

Although the reduction reaction using this catalyst may be conducted in a liquid phase or gas phase, the reduction reaction using this catalyst is preferably conducted in a liquid phase. Although the reduction reaction using this catalyst in a liquid phase may be conducted without using a solvent or in the presence of a solvent, the reduction reaction using this catalyst in a liquid phase is normally conducted in the presence of a solvent.

Examples of the solvent include, normally, water; lower alcohols, such as methanol and ethanol; alcohols that are the reaction products; ethers, such as tetrahydrofuran, dioxane, and ethylene glycol dimethyl ether; and hydrocarbons, such as hexane, decalin, and methylcyclohexane. The above solvents may be used alone or in a mixture of two or more.

In particular, in the case where a carbonyl compound is to be reduced, it is preferable to use a water solvent from the viewpoints of solubility and the like. The amount of the solvent used is normally, but not limited to, about 0.1 to 20 times by mass, is preferably 0.5 to 10 times by mass, and is more preferably about 1 to 10 times by mass the amount of the carbonyl compound used as a raw material.

The reduction reaction using this catalyst is normally conducted in a pressurized hydrogen gas. The reaction is normally conducted at 100° C. to 300° C. and is preferably conducted at 120° C. to 250° C. The reaction pressure is normally 1 to 30 MPaG, is preferably 1 to 25 MPaG, and is further preferably 5 to 25 MPaG.

After the reaction has been terminated, the product of the reduction reaction using this catalyst is normally recovered by solvent distillation, solvent distillation followed by extraction using an organic solvent, distillation, sublimation, crystallization, chromatography, or the like, which depends on the physical properties of the product. In the case where the product is liquid at handling temperature, it is preferable to recover the product while purifying the product by distillation. In the case where the product is solid at handling temperature, it is preferable to recover the product while purifying the product by crystallization. It is preferable to purify the solid product by washing.

EXAMPLES

The present invention is described below further in detail with reference to Examples. The present invention is not limited by Examples below without departing from the scope of the present invention.

(Measurement of Sulfate Ion Content)

A 0.2 M-aqueous sodium hydroxide solution was added to the sample. The resulting mixture was irradiated with ultrasonic wave and subsequently subjected to centrifugal separation. The resulting liquid was analyzed by ion chromatography in order to determine the content of sulfate ions in the sample.

(Measurement of Sulfur Content)

The content of sulfur in the sample was determined in accordance with a high-frequency furnace combustion-infrared detection method (carbon sulfur analyzer) by combusting the sample in a high-frequency induction heating furnace under an oxygen atmosphere and calculating the content of sulfur in the combustion gas by an infrared detection method.

Examples and Comparative Examples of First Invention

Example I-1

Ammonium perrhenate and tetraethoxygermanium(IV) were dissolved in water. Titanium oxide particles (Catalysis Society of Japan, Reference catalyst JRC-TIO-14 produced by Ishihara Sangyo Kaisha, Ltd.) having a specific surface area of 308 m²/g were added to the resulting solution. The solution was stirred at room temperature for 20 minutes. Subsequently, water was removed using an evaporator. Then, drying was performed at 100° C. for 4 hours. The resulting material was charged into a vertical baking tube. While air was passed through the tube, a baking treatment was performed at 500° C. for 3 hours. The resulting solid was charged into a vertical baking tube. While a hydrogen gas was passed through the tube, a reduction treatment was performed at 500° C. for 30 minutes. Subsequently, the temperature was reduced to 30° C. After purging with an argon gas had been performed, a 6-volume % oxygen/nitrogen gas was passed through the tube. Hereby, 5% rhenium-5% germanium/titanium oxide catalyst particles having stabilized surfaces (the ratio of the amount of rhenium supported to the total mass of the catalyst: 5 mass %, the ratio of the amount of germanium supported to the total mass of the catalyst: 5 mass % (Ge/Re=1)) were prepared. The sulfate ion contents in the titanium oxide particles (Catalysis Society of Japan, Reference catalyst JRC-TIO-14) and the catalyst were 0.2% by mass and 0.14% by mass, respectively. The sulfur content in the catalyst was 0.078% by mass.

Into a 70-mL high-pressure reactor, 100 mg of the catalyst prepared by the above method, 500 mg of sebacic acid, 2 g of water, and a stirrer chip were charged. After the reactor had been purged with nitrogen, a hydrogen gas (7 MPaG) was introduced into the reactor at room temperature. Subsequently, a hydrogenation reaction was conducted at 220° C. for 7.5 hours. The reaction pressure at 220° C. was 13 MPaG. After the reaction had been terminated, the temperature was reduced to room temperature and the pressure was then reduced. An analysis of the reaction liquid by gas chromatography confirmed that the molar yields of 1,10-decanediol and 10-hydroxydecanoic acid in the reaction were 5.9% and 48.1%, respectively, and the molar ratio of the by-products (1-nonanol, 1-decanol, 1-nonanoic acid, and 1-decanoic acid) to the target components (1,10-decanediol and 10-hydroxydecanoic acid) was 0.016.

Example I-2

A hydrogenation reaction was conducted as in Example I-1 with the catalyst prepared in Example I-1, except that the amount of time during which the hydrogenation reaction was conducted was changed to 18 hours. The molar yields of 1,10-decanediol and 10-hydroxydecanoic acid in the reaction were 89.3% and 6.5%, respectively. The molar ratio of the by-products (1-nonanol, 1-decanol, 1-nonanoic acid, and 1-decanoic acid) to the target components (1,10-decanediol and 10-hydroxydecanoic acid) was 0.017.

Example I-3

A hydrogenation reaction was conducted as in Example I-1 with a catalyst prepared as in Example I-1, except that the treatment in which the surfaces of the catalyst particles were stabilized by passing a 6-volume % oxygen/nitrogen gas through the tube was not performed after the reduction treatment had been performed while a hydrogen gas was passed through the tube. The molar yields of 1,10-decanediol and 10-hydroxydecanoic acid in the reaction were 74.7% and 2.6%, respectively. The molar ratio of the by-products (1-nonanol, 1-decanol, 1-nonanoic acid, and 1-decanoic acid) to the target components (1,10-decanediol and 10-hydroxydecanoic acid) was 0.004.

Example I-4

A 5% rhenium-5% germanium/titanium oxide catalyst was prepared by the same catalyst preparation method as in Example I-1, except that the titanium oxide particles were changed to titanium oxide particles having a specific surface area of 302 $m^2/g$ and a sulfate ion content of 4.8% by mass (MC-150, produced by Ishihara Sangyo Kaisha, Ltd.). The sulfate ion content in the catalyst was 0.63% by mass. The sulfur content in the catalyst was 0.57% by mass. A hydrogenation reaction was conducted as in Example I-1 with this catalyst. The molar yields of 1,10-decanediol and 10-hydroxydecanoic acid in the reaction were 81.7% and 0.6%, respectively. The molar ratio of the by-products (1-nonanol, 1-decanol, 1-nonanoic acid, and 1-decanoic acid) to the target components (10-hydroxydecanoic acid and 1,10-decanediol) was 0.006.

Example I-5

A 5% rhenium-5% germanium/titanium oxide catalyst was prepared by the same method as in Example I-1, except that the titanium oxide particles were changed to titanium oxide particles having a specific surface area of 90 $m^2/g$ and a sulfate ion content of 3.6% by mass (MC-90, produced by Ishihara Sangyo Kaisha, Ltd.). The sulfate ion content in the catalyst was 0.30% by mass. The sulfur content in the catalyst was 0.35% by mass. A hydrogenation reaction was conducted as in Example I-1 with this catalyst. The molar yields of 1,10-decanediol and 10-hydroxydecanoic acid in the reaction were 4.5% and 36.8%, respectively. The molar ratio of the by-products (1-nonanol, 1-decanol, 1-nonanoic acid, and 1-decanoic acid) to the target components (10-hydroxydecanoic acid and 1,10-decanediol) was 0.011.

Example I-6

A 5% rhenium-5% indium/titanium oxide catalyst was prepared by the same catalyst preparation method as in Example I-1, except that indium(III) chloride tetrahydrate was used instead of tetraethoxygermanium(IV). Subsequently, a hydrogenation reaction was conducted as in Example I-1. The molar yields of 1,10-decanediol and 10-hydroxydecanoic acid in the reaction were 9.0% and 43.5%, respectively. The molar ratio of the by-products (1-nonanol, 1-decanol, 1-nonanoic acid, and 1-decanoic acid) to the target components (10-hydroxydecanoic acid and 1,10-decanediol) was 0.034.

Example I-7

A 5% rhenium-5% silicon/titanium oxide catalyst was prepared by the same catalyst preparation method as in Example I-1, except that tetraethoxysilane(IV) was used instead of tetraethoxygermanium(IV) and ethanol was used instead of water for preparing the solution. Subsequently, a hydrogenation reaction was conducted as in Example I-1. The molar yields of 1,10-decanediol and 10-hydroxydecanoic acid in the reaction were 1.7% and 23.1%, respectively. The molar ratio of the by-products (1-nonanol, 1-decanol, 1-nonanoic acid, and 1-decanoic acid) to the target components (10-hydroxydecanoic acid and 1,10-decanediol) was 0.039.

Example I-8

A 5% rhenium-1% germanium/titanium oxide catalyst was prepared by the same catalyst preparation method as in Example I-1, except that the ratio between the amounts of ammonium perrhenate and tetraethoxygermanium(IV) used as metal raw materials was changed and the surfaces of the catalyst particles were not stabilized by passing the 6-volume % oxygen/nitrogen gas through the tube subsequent to the reduction treatment. A hydrogenation reaction was conducted as in Example I-1 with this catalyst, except that the amount of time during which the reaction was conducted was changed to 3 hours. The molar yields of 1,10-decanediol and 10-hydroxydecanoic acid in the reaction were 38.7% and 10.8%, respectively. The molar ratio of the by-products (1-nonanol, 1-decanol, 1-nonanoic acid, and 1-decanoic acid) to the target components (10-hydroxydecanoic acid and 1,10-decanediol) was 0.009.

Example I-9

A hydrogenation reaction was conducted with the catalyst prepared in Example I-3 as in Example I-1, except that the amount of time during which the reaction was conducted was changed to 3 hours. The molar yields of 1,10-decanediol and 10-hydroxydecanoic acid in the reaction were 35.3% and 32.9%, respectively. The molar ratio of the by-products (1-nonanol, 1-decanol, 1-nonanoic acid, and 1-decanoic acid) to the target components (10-hydroxydecanoic acid and 1,10-decanediol) was 0.005.

Example I-10

A 5% rhenium-5% germanium-0.5% ruthenium/titanium oxide catalyst was prepared by the same catalyst preparation method as in Example I-1, except that ammonium perrhenate, tetraethoxygermanium(IV), and ruthenium(III) chloride were used as metal raw materials and the surfaces of the catalyst particles were not stabilized by passing the 6-volume % oxygen/nitrogen gas through the tube subsequent to the reduction treatment. Subsequently, a hydrogenation reaction was conducted as in Example I-1. The molar yields of 1,10-decanediol and 10-hydroxydecanoic acid in the reaction were 72.0% and 3.6%, respectively. The molar ratio of the by-products (1-nonanol, 1-decanol, 1-nonanoic acid, and 1-decanoic acid) to the target components (10-hydroxydecanoic acid and 1,10-decanediol) was 0.006.

Example I-11

A 5% rhenium-5% germanium-5% ruthenium/titanium oxide catalyst was prepared by the same catalyst preparation method as in Example I-10, except that the ratio between the amounts of ammonium perrhenate, tetraethoxygermanium(IV), and ruthenium(III) chloride used as metal raw materials was changed. Subsequently, a hydrogenation reaction was conducted as in Example I-1. The molar yields of 1,10-decanediol and 10-hydroxydecanoic acid in the reaction were 89.0% and 0.4%, respectively. The molar ratio of the by-products (1-nonanol, 1-decanol, 1-nonanoic acid, and 1-decanoic acid) to the target components (10-hydroxydecanoic acid and 1,10-decanediol) was 0.020.

Comparative Example I-1

A 5% rhenium/titanium oxide catalyst was prepared by the same catalyst preparation method as in Example I-1, except that tetraethoxygermanium was not used. Subsequently, a hydrogenation reaction was conducted as in Example I-1. The molar yields of 1,10-decanediol and 10-hydroxydecanoic acid in the reaction were 0.1% and 21.0%, respectively. The molar ratio of the by-products (1-nonanol, 1-decanol, 1-nonanoic acid, and 1-decanoic acid) to the target components (1,10-decanediol and 10-hydroxydecanoic acid) was 0.060.

Comparative Example I-2

A 5% rhenium-5% palladium/titanium oxide catalyst was prepared by the same catalyst preparation method as in Example I-1, except that ammonium perrhenate and dichlorotetraamminepalladium(II) were used as metal raw materials. Subsequently, a hydrogenation reaction was conducted as in Example I-1. The molar yields of 1,10-decanediol and 10-hydroxydecanoic acid in the reaction were 33.1% and 0.0%, respectively. The molar ratio of the by-products (1-nonanol, 1-decanol, 1-nonanoic acid, and 1-decanoic acid) to the target components (10-hydroxydecanoic acid and 1,10-decanediol) was 0.825.

Comparative Example I-3

A 5% rhenium-5% ruthenium/titanium oxide catalyst was prepared by the same catalyst preparation method as in Example I-1, except that ammonium perrhenate and ruthenium(III) chloride were used as metal raw materials. Subsequently, a hydrogenation reaction was conducted as in Example I-1. The molar yields of 1,10-decanediol and 10-hydroxydecanoic acid in the reaction were 45.0% and 11.1%, respectively. The molar ratio of the by-products (1-nonanol, 1-decanol, 1-nonanoic acid, and 1-decanoic acid) to the target components (10-hydroxydecanoic acid and 1,10-decanediol) was 0.063.

Table 1 summarizes the results obtained in Examples I-1 to I-11 and Comparative examples I-1 to I-3.

TABLE 1

| | | | Reaction results | | |
| --- | --- | --- | --- | --- | --- |
| | Catalyst | Hydrogenation reaction time (hour) | Yield of 1,10-decanediol (mol %) | Yield of 10-hydroxydecanoic acid (mol %) | By-product/target component molar ratio |
| Example I-1 | 5% Re · 5% Ge/ $TiO_2$ | 7.5 | 5.9 | 48.1 | 0.016 |
| Example I-2 | 5% Re · 5% Ge/ $TiO_2$ | 18 | 89.3 | 6.5 | 0.017 |
| Example I-3 | 5% Re · 5% Ge/ $TiO_2$ | 7.5 | 74.7 | 2.6 | 0.004 |
| Example I-4 | 5% Re · 5% Ge/ $TiO_2$ | 7.5 | 31.7 | 0.6 | 0.006 |
| Example I-5 | 5% Re · 5% Ge/ $TiO_2$ | 7.5 | 4.5 | 36.8 | 0.011 |
| Example I-6 | 5% Re · 5% In/ $TiO_2$ | 7.5 | 9.0 | 43.5 | 0.034 |
| Example I-7 | 5% Re · 5% Si/ $TiO_2$ | 7.5 | 1.7 | 23.1 | 0.039 |

TABLE 1-continued

|  | Catalyst | Hydrogenation reaction time (hour) | Yield of 1,10-decanediol (mol %) | Yield of 10-hydroxydecanoic acid (mol %) | By-product/target component molar ratio |
|---|---|---|---|---|---|
| Example I-8 | 5% Re · 1% Ge/TiO$_2$ | 3 | 38.7 | 10.8 | 0.009 |
| Example I-9 | 5% Re · 5% Ge/TiO$_2$ | 3 | 35.3 | 32.9 | 0.005 |
| Example I-10 | 5% Re · 5% Ge · 0.5% Ru/TiO$_2$ | 7.5 | 72.0 | 3.6 | 0.006 |
| Example I-11 | 5% Re · 5% Ge · 5% Ru/TiO$_2$ | 7.5 | 89.0 | 0.4 | 0.020 |
| Comparative example I-1 | 5% Re/TiO$_2$ | 7.5 | 0.1 | 21.0 | 0.060 |
| Comparative example I-2 | 5% Re · 5% pd/TiO$_2$ | 7.5 | 33.1 | 0.0 | 0.825 |
| Comparative example I-3 | 5% Re · 5% Ru/TiO$_2$ | 7.5 | 45.0 | 11.1 | 0.063 |

Example I-12

Ammonium perrhenate and tetraethoxygermanium(IV) were dissolved in water. Titanium oxide particles (MC-150, produced by Ishihara Sangyo Kaisha, Ltd.) having a specific surface area of 302 m$^2$/g and a sulfate ion content of 4.8% by mass were added to the resulting solution. The solution was stirred at room temperature for 20 minutes. Subsequently, water was removed using an evaporator. Then, drying was performed at 100° C. for 4 hours. The resulting material was charged into a vertical baking tube. While air was passed through the tube, a baking treatment was performed at 500° C. for 3 hours. The resulting solid was charged into a vertical baking tube. While a hydrogen gas was passed through the tube, a reduction treatment was performed at 500° C. for 30 minutes. Hereby, a 5% rhenium-5% germanium/titanium oxide catalyst (the ratio of the amount of rhenium supported to the total mass of the catalyst: 5 mass %, the ratio of the amount of germanium supported to the total mass of the catalyst: 5 mass % (Ge/Re=1)) was prepared.

Into a 70-mL high-pressure reactor, 70 mg of the catalyst prepared by the above method, 260 mg of decanoic acid, 1.2 mL of methanol, and a stirrer chip were charged. After the reactor had been purged with nitrogen, a hydrogen gas (7 MPaG) was introduced into the reactor at room temperature. Subsequently, a hydrogenation reaction was conducted at 220° C. for 3 hours. The reaction pressure at 220° C. was 13 MPaG. After the reaction had been terminated, the temperature was reduced to room temperature and the pressure was then reduced. An analysis of the reaction liquid by gas chromatography confirmed that the molar yield of 10-decanol in the reaction was 76.5% and the molar ratio of the by-products (nonane and decane) to the target component (10-decanol) was 0.004.

Example I-13

A 5% rhenium-5% germanium/zirconium oxide catalyst was prepared by the same catalyst preparation method as in Example I-8, except that zirconium oxide particles having a specific surface area of 97 m$^2$/g which did not include a sulfate ion was used instead of the titanium oxide particles. Subsequently, a hydrogenation reaction was conducted as in Example I-8, except that a water solvent was used instead of methanol. The molar yield of 10-decanol in the reaction was 23.2% and the molar ratio of the by-products (nonane and decane) to the target component (10-decanol) was 0.001.

A comparison between the results obtained in Examples I-1 to I-11 and the results obtained in Comparative examples I-1 to 1-3, where a catalyst including a carrier composed of titanium oxide was used, confirms that using a catalyst produced by attaching the specific second component to a catalyst including rhenium and an oxide of a metal belonging to Group 4 of the periodic table increases the total amount of 1,10-decanediol and 10-hydroxydecanoic acid produced in a hydrogenation reaction of a carboxylic acid per unit specific surface area and enhances catalytic activity. Furthermore, the occurrence of side reactions, such as a defunctionalization reaction associated with dehydration and hydrogenation, can be markedly reduced. The advantageous effects become significant particularly when a catalyst including germanium is used. Note that, the total amount of 1,10-decanediol and 10-hydroxydecanoic acid produced is used as a measure of catalytic activity because 10-hydroxydecanoic acid is considered a reaction intermediate of the 1,10-decanediol product and can be derived into 1,10-decanediol when the reaction time is further prolonged. A comparison between the results obtained in Examples 1-12 and 1-13 confirms that a catalyst including a carrier composed of zirconium oxide also has the same advantageous effects as a catalyst including a carrier composed of titanium oxide. Specifically, it is confirmed that a catalyst including a zirconium oxide carrier has a catalytic activity comparable to that of a catalyst including a titanium oxide carrier in terms of catalytic activity per unit specific surface area. A comparison between the results obtained in Examples 1-1 and I-2 confirms that reaction selectivity can be maintained by using a catalyst that includes germanium even under high-inversion-rate reaction conditions, which have been an issue for rhenium catalysts. In addition, a comparison between the results obtained in Examples I-1, I-4, and I-5 confirms that the higher the sulfate ion content in the catalyst, the higher the degree of reduction in the defunctionalization reaction, the higher the reaction selectivity, and the higher the degree of increase in the catalytic activity of the hydrogenation catalyst per unit specific surface area of the carrier. The remarkable reduction in the side reactions enables the production of an alcohol with a high purity and a reduction in the costs of purification of the alcohol produced.

Examples and Comparative Examples of Second Invention

Example II-1

Ammonium perrhenate and tetraethoxygermanium(IV) were dissolved in water. Titanium oxide particles (Catalysis Society of Japan, Reference catalyst JRC-TIO-14 produced by Ishihara Sangyo Kaisha, Ltd.) having a specific surface area of 308 $m^2/g$ were added to the resulting solution. The solution was stirred at room temperature for 20 minutes. Subsequently, water was removed using an evaporator. Then, drying was performed at 100° C. for 4 hours. The resulting material was charged into a vertical baking tube. While air was passed through the tube, a baking treatment was performed at 500° C. for 3 hours. The resulting solid was charged into a vertical baking tube. While a hydrogen gas was passed through the tube, a reduction treatment was performed at 500° C. for 30 minutes. Subsequently, the temperature was reduced to 30° C. After purging with an argon gas had been performed, a 6-volume % oxygen/nitrogen gas was passed through the tube. Hereby, 5% rhenium-5% germanium/titanium oxide catalyst particles having stabilized surfaces (the ratio of the amount of rhenium supported to the total mass of the catalyst: 5 mass %, the ratio of the amount of germanium supported to the total mass of the catalyst: 5 mass % (Ge/Re=1)) were prepared. The sulfate ion contents in the titanium oxide particles (Catalysis Society of Japan, Reference catalyst JRC-TIO-14) and the catalyst were 0.2% by mass and 0.14% by mass, respectively. The sulfur content in the catalyst was 0.078% by mass.

Into a 70-mL high-pressure reactor, 100 mg of the catalyst prepared by the above method, 500 mg of sebacic acid, 2 g of water, and a stirrer chip were charged. After the reactor had been purged with nitrogen, a hydrogen gas (7 MPaG) was introduced into the reactor at room temperature. Subsequently, a hydrogenation reaction was conducted at 220° C. for 7.5 hours. The reaction pressure at 220° C. was 13 MPaG. After the reaction had been terminated, the temperature was reduced to room temperature and the pressure was then reduced. An analysis of the reaction liquid by gas chromatography confirmed that the molar yields of 1,10-decanediol and 10-hydroxydecanoic acid in the reaction were 5.9% and 48.1%, respectively, and the molar ratio of the by-products (1-nonanol, 1-decanol, 1-nonanoic acid, and 1-decanoic acid) to the target components (1,10-decanediol and 10-hydroxydecanoic acid) was 0.016.

Example II-2

A hydrogenation reaction was conducted as in Example II-1 with the catalyst prepared in Example II-1, except that the amount of time during which the hydrogenation reaction was conducted was changed to 18 hours. The molar yields of 1,10-decanediol and 10-hydroxydecanoic acid in the reaction were 89.3% and 6.5%, respectively. The molar ratio of the by-products (1-nonanol, 1-decanol, 1-nonanoic acid, and 1-decanoic acid) to the target components (1,10-decanediol and 10-hydroxydecanoic acid) was 0.017.

Example II-3

A hydrogenation reaction was conducted as in Example II-1 with a catalyst prepared as in Example II-1, except that the treatment in which the surfaces of the catalyst particles were stabilized by passing a 6-volume % oxygen/nitrogen gas through the tube was not performed after the reduction treatment had been performed while a hydrogen gas was passed through the tube. The molar yields of 1,10-decanediol and 10-hydroxydecanoic acid in the reaction were 74.7% and 2.6%, respectively. The molar ratio of the by-products (1-nonanol, 1-decanol, 1-nonanoic acid, and 1-decanoic acid) to the target components (1,10-decanediol and 10-hydroxydecanoic acid) was 0.004.

Example II-4

A 5% rhenium-5% germanium/titanium oxide catalyst was prepared by the same catalyst preparation method as in Example II-1, except that the titanium oxide particles were changed to titanium oxide particles having a specific surface area of 302 $m^2/g$ and a sulfate ion content of 4.8% by mass (MC-150, produced by Ishihara Sangyo Kaisha, Ltd.). The sulfate ion content in the catalyst was 0.63% by mass. The sulfur content in the catalyst was 0.57% by mass. A hydrogenation reaction was conducted as in Example II-1 with this catalyst. The molar yields of 1,10-decanediol and 10-hydroxydecanoic acid in the reaction were 81.7% and 0.6%, respectively. The molar ratio of the by-products (1-nonanol, 1-decanol, 1-nonanoic acid, and 1-decanoic acid) to the target components (10-hydroxydecanoic acid and 1,10-decanediol) was 0.006.

Example II-5

A 5% rhenium-5% germanium/titanium oxide catalyst was prepared by the same method as in Example II-1, except that the titanium oxide particles were changed to titanium oxide particles having a specific surface area of 90 $m^2/g$ and a sulfate ion content of 3.6% by mass (MC-90, produced by Ishihara Sangyo Kaisha, Ltd.). The sulfate ion content in the catalyst was 0.30% by mass. The sulfur content in the catalyst was 0.35% by mass. A hydrogenation reaction was conducted as in Example II-1 with this catalyst. The molar yields of 1,10-decanediol and 10-hydroxydecanoic acid in the reaction were 4.5% and 36.8%, respectively. The molar ratio of the by-products (1-nonanol, 1-decanol, 1-nonanoic acid, and 1-decanoic acid) to the target components (10-hydroxydecanoic acid and 1,10-decanediol) was 0.011.

Example II-6

A 5% rhenium-5% indium/titanium oxide catalyst was prepared by the same catalyst preparation method as in Example II-1, except that indium(III) chloride tetrahydrate was used instead of tetraethoxygermanium(IV). Subsequently, a hydrogenation reaction was conducted as in Example II-1. The molar yields of 1,10-decanediol and 10-hydroxydecanoic acid in the reaction were 9.0% and 43.5%, respectively. The molar ratio of the by-products (1-nonanol, 1-decanol, 1-nonanoic acid, and 1-decanoic acid) to the target components (10-hydroxydecanoic acid and 1,10-decanediol) was 0.034.

Example II-7

A 5% rhenium-5% silicon/titanium oxide catalyst was prepared by the same catalyst preparation method as in Example II-1, except that tetraethoxysilane(IV) was used instead of tetraethoxygermanium(IV) and ethanol was used instead of water for preparing the solution. Subsequently, a hydrogenation reaction was conducted as in Example II-1. The molar yields of 1,10-decanediol and 10-hydroxydecanoic acid in the reaction were 1.7% and 23.1%, respectively. The molar ratio of the by-products (1-nonanol, 1-decanol, 1-nonanoic acid, and 1-decanoic acid) to the target components (10-hydroxydecanoic acid and 1,10-decanediol) was 0.039.

Example II-8

A 5% rhenium-1% germanium/titanium oxide catalyst was prepared by the same catalyst preparation method as in Example II-1, except that the ratio between the amounts of ammonium perrhenate and tetraethoxygermanium(IV) used as metal raw materials was changed and the surfaces of the catalyst particles were not stabilized by passing the 6-volume % oxygen/nitrogen gas through the tube subsequent to the reduction treatment. A hydrogenation reaction was conducted as in Example II-1 with this catalyst, except that the amount of time during which the reaction was conducted was changed to 3 hours. The molar yields of 1,10-decanediol and 10-hydroxydecanoic acid in the reaction were 38.7% and 10.8%, respectively. The molar ratio of the by-products (1-nonanol, 1-decanol, 1-nonanoic acid, and 1-decanoic acid) to the target components (10-hydroxydecanoic acid and 1,10-decanediol) was 0.009.

Example II-9

A hydrogenation reaction was conducted with the catalyst prepared in Example II-3 as in Example II-1, except that the amount of time during which the reaction was conducted was changed to 3 hours. The molar yields of 1,10-decanediol and 10-hydroxydecanoic acid in the reaction were 35.3% and 32.9%, respectively. The molar ratio of the by-products (1-nonanol, 1-decanol, 1-nonanoic acid, and 1-decanoic acid) to the target components (10-hydroxydecanoic acid and 1,10-decanediol) was 0.005.

Example II-10

A 5% rhenium-5% germanium-0.5% ruthenium/titanium oxide catalyst was prepared by the same catalyst preparation method as in Example II-1, except that ammonium perrhenate, tetraethoxygermanium(IV), and ruthenium(III) chloride were used as metal raw materials and the surfaces of the catalyst particles were not stabilized by passing the 6-volume % oxygen/nitrogen gas through the tube subsequent to the reduction treatment. Subsequently, a hydrogenation reaction was conducted as in Example II-1. The molar yields of 1,10-decanediol and 10-hydroxydecanoic acid in the reaction were 72.0% and 3.6%, respectively. The molar ratio of the by-products (1-nonanol, 1-decanol, 1-nonanoic acid, and 1-decanoic acid) to the target components (10-hydroxydecanoic acid and 1,10-decanediol) was 0.006.

Example II-11

A 5% rhenium-5% germanium-5% ruthenium/titanium oxide catalyst was prepared by the same catalyst preparation method as in Example II-10, except that the ratio between the amounts of ammonium perrhenate, tetraethoxygermanium(IV), and ruthenium(III) chloride used as metal raw materials was changed. Subsequently, a hydrogenation reaction was conducted as in Example II-1. The molar yields of 1,10-decanediol and 10-hydroxydecanoic acid in the reaction were 89.0% and 0.4%, respectively. The molar ratio of the by-products (1-nonanol, 1-decanol, 1-nonanoic acid, and 1-decanoic acid) to the target components (10-hydroxydecanoic acid and 1,10-decanediol) was 0.020.

Comparative Example II-1

A 5% rhenium/titanium oxide catalyst was prepared by the same catalyst preparation method as in Example II-1, except that tetraethoxygermanium was not used. Subsequently, a hydrogenation reaction was conducted as in Example II-1. The molar yields of 1,10-decanediol and 10-hydroxydecanoic acid in the reaction were 0.1% and 21.0%, respectively. The molar ratio of the by-products (1-nonanol, 1-decanol, 1-nonanoic acid, and 1-decanoic acid) to the target components (1,10-decanediol and 10-hydroxydecanoic acid) was 0.060.

Comparative Example II-2

A 5% rhenium-5% palladium/titanium oxide catalyst was prepared by the same catalyst preparation method as in Example II-1, except that ammonium perrhenate and dichlorotetraamminepalladium(II) were used as metal raw materials. Subsequently, a hydrogenation reaction was conducted as in Example I-1. The molar yields of 1,10-decanediol and 10-hydroxydecanoic acid in the reaction were 33.1% and 0.0%, respectively. The molar ratio of the by-products (1-nonanol, 1-decanol, 1-nonanoic acid, and 1-decanoic acid) to the target components (10-hydroxydecanoic acid and 1,10-decanediol) was 0.825.

Comparative Example II-3

A 5% rhenium-5% ruthenium/titanium oxide catalyst was prepared by the same catalyst preparation method as in Example II-1, except that ammonium perrhenate and ruthenium(III) chloride were used as metal raw materials. Subsequently, a hydrogenation reaction was conducted as in Example II-1. The molar yields of 1,10-decanediol and 10-hydroxydecanoic acid in the reaction were 45.0% and 11.1%, respectively. The molar ratio of the by-products (1-nonanol, 1-decanol, 1-nonanoic acid, and 1-decanoic acid) to the target components (10-hydroxydecanoic acid and 1,10-decanediol) was 0.063.

Table 2 summarizes the results obtained in Examples II-1 to II-11 and Comparative examples II-1 to II-3.

TABLE 2

|  | Catalyst | Hydrogenation reaction time (hour) | Yield of 1,10-decanediol (mol %) | Yield of 10-hydroxydecanoic acid (mol %) | By-product/target component molar ratio |
|---|---|---|---|---|---|
| Example II-1 | 5% Re · 5% Ge/TiO$_2$ | 7.5 | 5.9 | 48.1 | 0.016 |
| Example II-2 | 5% Re · 5% Ge/TiO$_2$ | 18 | 89.3 | 6.5 | 0.017 |
| Example II-3 | 5% Re · 5% Ge/TiO$_2$ | 7.5 | 74.7 | 2.6 | 0.004 |
| Example II-4 | 5% Re · 5% Ge/TiO$_2$ | 7.5 | 81.7 | 0.6 | 0.006 |
| Example II-5 | 5% Re · 5% Ge/TiO$_2$ | 7.5 | 4.5 | 36.8 | 0.011 |
| Example II-6 | 5% Re · 5% In/TiO$_2$ | 7.5 | 9.0 | 43.5 | 0.034 |
| Example II-7 | 5% Re · 5% Si/TiO$_2$ | 7.5 | 1.7 | 23i | 0.039 |
| Example II-8 | 5% Re · 1% Ge/TiO$_2$ | 3 | 38.7 | 10.8 | 0.009 |
| Example II-9 | 5% Re · 5% Ge/TiO$_2$ | 3 | 35.3 | 32.9 | 0.005 |
| Example II-10 | 5% Re · 5% Ge · 0.5% Ru/TiO$_2$ | 7.5 | 72.0 | 3.6 | 0.006 |
| Example II-11 | 5% Re · 5% Ge · 5% Ru/TiO$_2$ | 7.5 | 89.0 | 0.4 | 0.020 |
| Comparative example II-1 | 5% Re/TiO$_2$ | 7.5 | 0.1 | 21.0 | 0.060 |
| Comparative example II-2 | 5% Re · 5% pd/TiO$_2$ | 7.5 | 33.1 | 0.0 | 0.825 |
| Comparative example II-3 | 5% Re · 5% Ru/TiO$_2$ | 7.5 | 45.0 | 11.1 | 0.063 |

Example II-12

Ammonium perrhenate and tetraethoxygermanium(IV) were dissolved in water. Titanium oxide particles (MC-150, produced by Ishihara Sangyo Kaisha, Ltd.) having a specific surface area of 302 m$^2$/g and a sulfate ion content of 4.8% by mass were added to the resulting solution. The solution was stirred at room temperature for 20 minutes. Subsequently, water was removed using an evaporator. Then, drying was performed at 100° C. for 4 hours. The resulting material was charged into a vertical baking tube. While air was passed through the tube, a baking treatment was performed at 500° C. for 3 hours. The resulting solid was charged into a vertical baking tube. While a hydrogen gas was passed through the tube, a reduction treatment was performed at 500° C. for 30 minutes. Hereby, a 5% rhenium-5% germanium/titanium oxide catalyst (the ratio of the amount of rhenium supported to the total mass of the catalyst: 5 mass %, the ratio of the amount of germanium supported to the total mass of the catalyst: 5 mass % (Ge/Re=1)) was prepared.

Into a 70-mL high-pressure reactor, 70 mg of the catalyst prepared by the above method, 260 mg of decanoic acid, 1.2 mL of methanol, and a stirrer chip were charged. After the reactor had been purged with nitrogen, a hydrogen gas (7 MPaG) was introduced into the reactor at room temperature. Subsequently, a hydrogenation reaction was conducted at 220° C. for 3 hours. The reaction pressure at 220° C. was 13 MPaG. After the reaction had been terminated, the temperature was reduced to room temperature and the pressure was then reduced. An analysis of the reaction liquid by gas chromatography confirmed that the molar yield of 10-decanol in the reaction was 76.5% and the molar ratio of the by-products (nonane and decane) to the target component (10-decanol) was 0.004.

Example II-13

A 5% rhenium-5% germanium/zirconium oxide catalyst was prepared by the same catalyst preparation method as in Example II-8, except that zirconium oxide particles having a specific surface area of 97 m$^2$/g which did not include a sulfate ion was used instead of the titanium oxide particles. Subsequently, a hydrogenation reaction was conducted as in Example II-8, except that a water solvent was used instead of methanol. The molar yield of 10-decanol in the reaction was 23.2% and the molar ratio of the by-products (nonane and decane) to the target component (10-decanol) was 0.001.

A comparison between the results obtained in Examples II-1 to II-11 and the results obtained in Comparative examples II-1 to 11-3, where a catalyst including a carrier composed of titanium oxide was used, confirms that using a catalyst including rhenium and a specific amount of second component increases the total amount of 1,10-decanediol and 10-hydroxydecanoic acid produced in a hydrogenation reaction of a carboxylic acid per unit specific surface area and enhances catalytic activity per unit specific surface area. Furthermore, the occurrence of side reactions, such as a defunctionalization reaction associated with dehydration and hydrogenation, can be markedly reduced. The advantageous effects become significant particularly when a catalyst including germanium is used. Note that, the total amount of 1,10-decanediol and 10-hydroxydecanoic acid produced is used as a measure of catalytic activity because 10-hydroxydecanoic acid is considered a reaction intermediate of the 1,10-decanediol product and can be derived into 1,10-decanediol when the reaction time is further prolonged. A comparison between the results obtained in Examples II-12 and II-13 confirms that a catalyst including a carrier composed of zirconium oxide also has the same advantageous effects as a catalyst including a carrier composed of titanium oxide.

Specifically, it is confirmed that a catalyst including a zirconium oxide carrier has a catalytic activity comparable to that of a catalyst including a titanium oxide carrier in terms of catalytic activity per unit specific surface area. A comparison between the results obtained in Examples II-1 and 11-2 confirms that reaction selectivity can be maintained by using a catalyst that includes germanium even under high-inversion-rate reaction conditions, which have been an issue for rhenium catalysts. In addition, a comparison between the results obtained in Examples II-1, II-4, and II-5 confirms that the higher the sulfate ion content in the catalyst, the higher the degree of reduction in the defunctionalization reaction, the higher the reaction selectivity, and the higher the degree of increase in the catalytic activity of the hydrogenation catalyst per unit specific surface area of the carrier. The remarkable reduction in the side reactions enables the production of an alcohol with a high purity and a reduction in the costs of purification of the alcohol produced.

INDUSTRIAL APPLICABILITY

This catalyst is industrially useful as a catalyst for directly synthesizing an alcohol from a carbonyl compound. This catalyst enables an intended alcohol to be produced with high activity and high selectivity and reduces increases in the costs of purification of the product and the costs of production of the catalyst. Therefore, this catalyst is industrially highly valuable.

Although the present invention has been described in detail with reference to particular embodiments, it is apparent to a person skilled in the art that various modifications can be made therein without departing from the spirit and scope of the present invention.

The present application is based on Japanese Patent Application No. 2017-043988 filed on Mar. 8, 2017, and Japanese Patent Application No. 2017-102053 filed on May 23, 2017, which are incorporated herein by reference in their entirety.

The invention claimed is:

1. An alcohol production method in which an alcohol is produced from a carbonyl compound, the method comprising producing the alcohol by contacting the carbonyl compound with a catalyst, the catalyst comprising a metal component comprising a first component that is rhenium and one or more second components selected from the group consisting of silicon, gallium, germanium, and indium and a carrier on which the metal component is supported, the carrier comprising an oxide of a metal belonging to Group 4 of the periodic table.

2. The alcohol production method according to claim 1, wherein a mass ratio of elements that are the second components included in the catalyst to the rhenium element included in the catalyst is in a range of 0.1 to 10.

3. The alcohol production method according to claim 1, wherein the oxide of a metal belonging to Group 4 of the periodic table, the oxide being included in the catalyst, comprises titanium oxide and/or zirconium oxide.

4. The alcohol production method according to claim 1, wherein the catalyst is prepared by a method comprising attaching the metal component to the carrier, wherein the carrier further comprises a sulfate ion.

5. The alcohol production method according to claim 4, wherein the sulfate ion content in the carrier is 0.01% by mass to 10% by mass of the mass of the carrier.

6. The alcohol production method according to claim 4, wherein the sulfate ion content in the catalyst is 0.01% by mass to 10% by mass of the mass of the catalyst.

7. A method of hydrogenating a carbonyl compound to a corresponding alcohol, the method comprising:
producing the corresponding alcohol by contacting the carbonyl compound with a catalyst, the catalyst comprising a metal component comprising a first component that is rhenium and one or more second components selected from the group consisting of silicon, gallium, germanium, and indium and a carrier on which the metal component is supported, the carrier comprising an oxide of a metal belonging to Group 4 of the periodic table.

8. The method according to claim 7, wherein the carbonyl compound is at least one selected from the group consisting of a carboxylic acid, a carboxylic acid ester, a carboxylic anhydride, and an aldehyde.

9. The method according to claim 7, wherein the carbonyl compound is a polyvalent carboxylic acid, and the corresponding alcohol is a hydroxycarboxylic acid or a polyhydric alcohol.

10. The method according to claim 7, wherein a mass ratio of elements that are the second components included in the catalyst to the rhenium element included in the catalyst is in a range of 0.1 to 10.

11. The method according to claim 7, wherein the oxide of a metal belonging to Group 4 of the periodic table, the oxide being included in the catalyst, comprises titanium oxide and/or zirconium oxide.

12. The method according to claim 7, wherein the catalyst is prepared by a method comprising attaching the metal component to the carrier, wherein the carrier further comprises a sulfate ion.

13. The method according to claim 12, wherein the sulfate ion content in the carrier is 0.01% by mass to 10% by mass of the mass of the carrier.

14. The method according to claim 12, wherein the sulfate ion content in the catalyst is 0.01% by mass to 10% by mass of the mass of the catalyst.

15. The method according to claim 7, wherein the method provides a molar ratio of a difunctionalized by-product to the corresponding alcohol of less than 0.060.

16. The method according to claim 15, wherein the molar ratio of the difunctionalized by-product to the corresponding alcohol is from 0.004 to 0.039.

* * * * *